(12) United States Patent
Mouri et al.

(10) Patent No.: US 9,821,144 B2
(45) Date of Patent: Nov. 21, 2017

(54) DIRECTION CHANGING DEVICE, MEDICAL ASSEMBLY HAVING THE SAME, AND METHOD

(71) Applicants: Takayuki Mouri, Shizuoka (JP); Hiroshi Yagi, Shizuoka (JP)

(72) Inventors: Takayuki Mouri, Shizuoka (JP); Hiroshi Yagi, Shizuoka (JP)

(73) Assignee: TERUMO KABUSHIKI KAISHA (JP)

( * ) Notice: Subject to any disclaimer, the term of this patent is extended or adjusted under 35 U.S.C. 154(b) by 798 days.

(21) Appl. No.: 13/763,423

(22) Filed: Feb. 8, 2013

(65) Prior Publication Data
US 2013/0211382 A1  Aug. 15, 2013

(30) Foreign Application Priority Data

Feb. 10, 2012  (JP) .................................. 2012-27182
Feb. 10, 2012  (JP) .................................. 2012-27185
Sep. 21, 2012  (JP) .................................. 2012-208506

(51) Int. Cl.
*A61M 25/01* (2006.01)
*A61M 25/02* (2006.01)

(52) U.S. Cl.
CPC ........ *A61M 25/0133* (2013.01); *A61M 25/01* (2013.01); *A61M 25/02* (2013.01); *A61M 2025/024* (2013.01)

(58) Field of Classification Search
CPC .. A61M 25/01; A61M 25/0133; A61M 25/02; A61M 2025/024; A61M 2025/028
(Continued)

(56) References Cited

U.S. PATENT DOCUMENTS 3,942,528 A   3/1976  Loeser
4,027,668 A   6/1977  Dunn
(Continued)

FOREIGN PATENT DOCUMENTS

CN   1089167 A      7/1994
DE   198 40 003 A1  3/1999
(Continued)

OTHER PUBLICATIONS

Chinese Office Action dated May 26, 2014, issued in the corresponding Chinese patent application No. 201210501955.6.
(Continued)

*Primary Examiner* — Laura Bouchelle
(74) *Attorney, Agent, or Firm* — Fitch Even Tabin & Flannery LLP

(57) ABSTRACT

In one form, a direction changing device is provided including: a first mounting section; and a second mounting section, wherein an axial direction of the first mounting section and an axial direction of the second mounting section intersect each other or are parallel to each other in plan view, and in a condition where a catheter or a sheath introducer in which the catheter is inserted is mounted to the first mounting section and the second mounting section, the catheter or the sheath introducer adopts a curved shape such that a catheter or sheath introducer portion mounted to the first mounting section extends proximally to distally in one direction and a catheter or sheath introducer portion mounted to the second mounting section extends proximally to distally in another direction with the directions being different from each other.

8 Claims, 35 Drawing Sheets

(58) Field of Classification Search
USPC .......................................................... 604/174
See application file for complete search history.

(56) References Cited

U.S. PATENT DOCUMENTS

| | | | | |
|---|---|---|---|---|
| 5,916,199 | A * | 6/1999 | Miles | A61M 25/02 604/174 |
| 6,001,081 | A * | 12/1999 | Collen | A61M 25/00 604/174 |
| 7,198,066 | B2 * | 4/2007 | Kagenow | A61M 25/02 128/DIG. 26 |
| 7,678,083 | B2 * | 3/2010 | Stephens | A61M 5/1418 206/364 |
| D743,541 | S * | 11/2015 | Serafini | D24/128 |
| 2005/0137580 | A1 | 6/2005 | Raulerson et al. | |
| 2005/0234405 | A1 | 10/2005 | Dikeman et al. | |
| 2006/0047268 | A1 | 3/2006 | Stephens | |

FOREIGN PATENT DOCUMENTS

| | | |
|---|---|---|
| JP | S52-097286 | 8/1977 |
| JP | H03-168159 A | 7/1991 |
| WO | 99/56802 A1 | 11/1999 |
| WO | 02/061318 A1 | 8/2002 |
| WO | 2004/095666 A1 | 11/2004 |
| WO | 2011/084505 A2 | 7/2011 |

OTHER PUBLICATIONS

European Communication pursuant to Article 94(3) EPC issued in corresponding European Application No. 13 154 288.8, dated Mar. 4, 2014 (7 pages).
European Communication pursuant to Article 94(3) EPC issued in corresponding European Application No. 13 154 288.8, dated Jun. 24, 2014 (6 pages).
Extended European Search Report and European Search Opinion issued in counterpart European Application No. 13 154 288.8, dated May 2, 2013 (7 pages).
Office Action issued in corresponding Japanese Patent Application No. 2012-208506 dated Feb. 2, 2016 (3 pages).

* cited by examiner

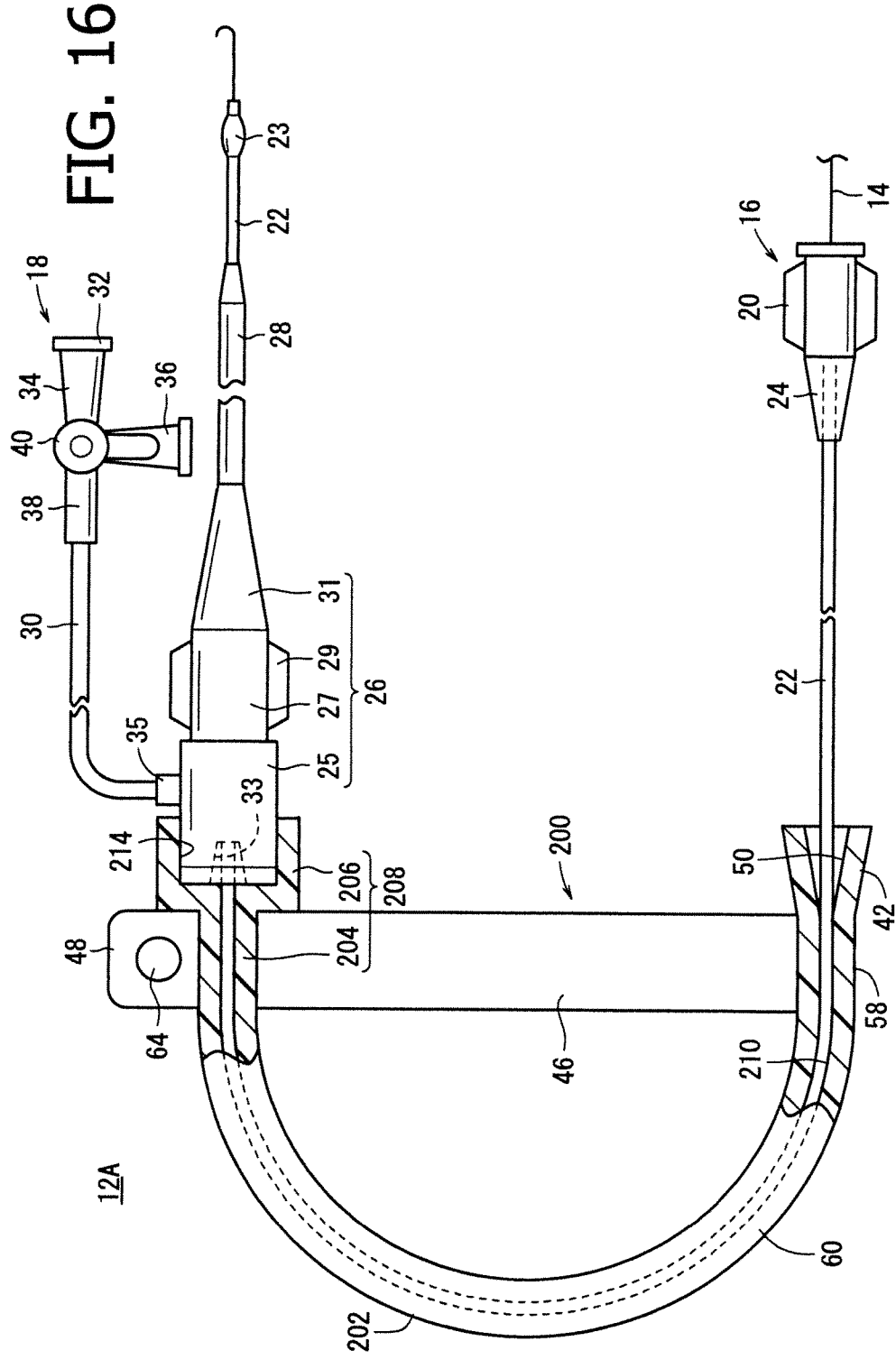

DIRECTION CHANGING DEVICE, MEDICAL ASSEMBLY HAVING THE SAME, AND METHOD

CROSS-REFERENCE TO RELATED APPLICATIONS

This application claims priority of Japanese Patent Application JP 2012-27185 filed on Feb. 10, 2012, Japanese Patent Application JP 2012-27182 filed on Feb. 10, 2012, and Japanese Patent Application JP 2012-208506 filed on Sep. 21, 2012, which are hereby incorporated herein by reference in their entirety.

FIELD OF THE INVENTION

The present invention relates to a direction changing device to be mounted to a catheter or a sheath introducer through which the catheter is passed, a medical assembly having the direction changing device, and method of using such a medical assembly.

BACKGROUND OF THE INVENTION

Conventionally, it has been a common practice to insert a catheter into a organ of a living body such as a blood vessel to deliver the catheter's distal portion to a lesion (for example, a stenosed part), and perform diagnosis or treatment on the lesion.

Specifically, as a method of percutaneously inserting a catheter into a blood vessel, there has been known the sheath method based on the use of a sheath introducer. In the sheath method, a sheath tube of the sheath introducer is preliminarily inserted into a blood vessel, and, with the sheath tube kept in place, a catheter is inserted into the blood vessel through the lumen of the sheath tube (see, for example, Japanese Patent Laid-open No. Hei 03-168159, hereinafter referred to also as Patent Document 1). Such a method ensures that even in the case of, for example, inserting a large-diameter catheter (e.g., a balloon catheter) into a blood vessel, damage to the blood vessel can be minimized.

Ordinarily, a sheath introducer has a sheath hub connected to the proximal end of the sheath tube, and a catheter insertion port through which the catheter can be inserted, opens to the proximal end face of the sheath hub. In the condition where the sheath tube is set in place in a blood vessel, therefore, the catheter insertion port is oriented to face in a direction opposite to the direction of insertion of the sheath tube into the blood vessel. In other words, the direction of insertion of the sheath tube into the blood vessel and the direction of insertion of the catheter into the sheath introducer coincide with each other.

SUMMARY OF THE INVENTION

Meanwhile, in an operating room, the operator ordinarily stands at the right side of a patient lying supine on an operating table, while manipulating a medical apparatus such as a catheter. Therefore, for example in the case where the direction of insertion of the sheath tube into the living body is rightward with respect to the operator who stands facing the patient, it is difficult for the operator to manipulate the catheter with their right hand to insert the catheter into the sheath introducer.

On the other hand, for example where the direction of insertion of the sheath tube into the living body is leftward with respect to the operator who stands facing the patient, it is difficult for the operator to operate the catheter with their left hand to insert the catheter into the sheath introducer.

As a result, depending on the direction in which the sheath tube is inserted into the living body, the operator may be forced, when inserting the catheter into the sheath introducer, to manipulate the catheter by the hand that is other than the operator's dominant hand. This may make it very difficult for the operator to efficiently insert the catheter into the living body.

The present invention has been made in consideration of the above-mentioned problem. Accordingly, it is an object of the present invention to provide a direction changing device which ensures that at the time of inserting a catheter into a sheath introducer, the operator can easily manipulate the catheter by the operator's dominant hand, irrespective of the direction of insertion of the sheath introducer into a living body, so that the catheter can be inserted into the living body in an efficient manner. It is another object of the invention to provide a medical assembly provided with the direction changing device.

The present invention is concerned with the following.

In one form, a direction changing device for use with a flexible tubular medical device is provided. Herein, a flexible tubular medical device can include catheters and sheath introducers, as well as other medical devices having a flexible, tubular construction. The direction changing device includes a first mounting section that generally extends in first axial direction and being configured to allow a first portion of the tubular medical device to be received therein; and a second mounting section that generally extends in a second axial direction and being configured to allow a second portion of the tubular medical device to be received therein, the first and second mounting sections being fixed in spaced relation to each other with the first and second axial directions generally extending in a plane either transverse or parallel to each other so that with the tubular medical device portions received therein, the first and second portions will extend in either transverse or parallel directions to each other.

In the above form, the first and second mounting sections can be configured so that with the corresponding tubular medical device first and second portions received therein, the tubular medical device adopts a curved configuration extending between the first and second mounting sections so that the first and second portions extend in parallel and in opposite directions to each other.

In the above form, an interconnecting section can be provided extending between the first and second mounting sections configured to fix the first and second mounting sections in spaced relation to each other.

In the above form, one of the first and second mounting sections can be removably connected to the interconnecting section at at least one location therealong.

In the above form, the first and second mounting sections can have an arcuate intermediate section extending therebetween so that the tubular medical device adopts a curved configuration when received in the arcuate intermediate section and with the first and second portions received in the corresponding first and second mounting sections. In the above form, the first and second mounting sections can each have an axial slit therein to allow the first and second portions of the tubular medical device to be received therein.

In the above form, the slits can be configured so that the tubular medical device portions are received by a snap-fit connection in the respective mounting sections.

The above form can be provided in combination with the tubular medical device.

In another form, a medical assembly is provided including a catheter having a shaft; a sheath introducer having a sheath tube for being inserted into a blood vessel and for receiving the catheter shaft to be advanced into the blood vessel; and a redirecting mechanism configured for receiving at least one of the catheter shaft and the sheath tube therein and configured to allow an operator to direct the catheter shaft in a first direction via a first end portion of the redirecting mechanism with the catheter shaft exiting the redirecting mechanism in a second direction via a second end portion thereof for being inserted into the blood vessel.

In the above form, the redirecting mechanism end portions can be spaced tubular portions configured to receive predetermined portions of the at least one of the catheter shaft and sheath tube therein, and connecting structure can extend between the spaced tubular portions that is configured for substantially fixing the spacing between the tubular portions.

In the above form, at least one of the predetermined portions of the at least one of the catheter shaft and the sheath tube can be received in a corresponding one of the spaced tubular portions by a snap-fit connection therebetween.

In the above form, the redirecting mechanism can have a tubular body including the spaced tubular portions, and the tubular body can further have an intermediate portion extending between the spaced tubular portion with the intermediate portion having an arcuate configuration.

In the above form, the sheath introducer can include a hub that is enlarged relative to the sheath tube, and one of the intermediate portion and a predetermined one of the tubular portions can be enlarged for receiving the enlarged hub therein.

In the above form, at least one of the tubular portions and the connecting structure can have a removable connection therebetween to allow adjacent portions of the tubular body to the one tubular portion to be removably connected to the connecting structure via the removable connection for adjusting the curvature of the intermediate portion.

In the above form, the connecting structure can have a generally elongate plate body, and one of the tubular portions can be generally formed in the plate body.

In the above form, the tubular portions and connecting structure can be integrally formed as a one-piece unitary component.

In the above form, at least one of the tubular portions and the connecting structure can have a plurality of removable connections therebetween.

In the above form, the redirecting mechanism can be configured such that the first and second directions are substantially opposite to each other.

In another aspect, a method of inserting a tubular medical device into an organ of a patient is provided including guiding the tubular medical device to be advanced in a first direction as the tubular medical device is manipulated by an operator to be directed in the first direction; and guiding the tubular medical device to be advanced in a second direction different than the first direction as the tubular medical device continues to be manipulated by the operator to be directed in the first direction.

The tubular medical device can be guided to be advanced in the first and second directions by end portions of a tubular body, and the end portions can be arranged so that the first and second directions are substantially opposite to each other.

Other forms of the invention are discussed below. [1] A direction changing device to be mounted to a catheter or to a sheath introducer in which the catheter is inserted, the direction changing device including: a first mounting section capable of being mounted to a part of the catheter or a part of the sheath introducer; and a second mounting section capable of being mounted to another part of the catheter or another part of the sheath introducer, wherein an axial direction of the first mounting section and an axial direction of the second mounting section intersect each other or are parallel to each other in plan view, and in a condition where the catheter or the sheath introducer is mounted to the first mounting section and the second mounting section, the catheter or the sheath introducer adopts a curved shape such that a catheter or sheath introducer portion mounted to the first mounting section extends proximally to distally in one direction and a catheter or sheath introducer portion mounted to the second mounting section extends proximally to distally in another direction with the directions being different from each other.

According to the direction changing device configured as above, the axial direction of the first mounting section and the axial direction of the second mounting section intersect each other or are parallel to each other in plan view, and, in the condition where a catheter or a sheath introducer is mounted to the first mounting section and the second mounting section, the catheter or the sheath introducer is put in a curved shape such that the first direction and the second direction are different from each other. Therefore, the direction of insertion of the sheath introducer into a living body and the direction of insertion of the catheter into the sheath introducer can be easily made different from each other. This ensures that at the time of inserting the catheter into the sheath introducer, the catheter can be easily operated by the operator's dominant hand. Consequently, the catheter can be efficiently inserted into the living body.

[2] In the direction changing device as above, a configuration may be adopted wherein in the condition where the catheter or the sheath introducer is mounted to the first mounting section and the second mounting section, the catheter or the sheath introducer is put in a curved shape such that the first direction and the second direction are substantially opposite to each other.

According to this configuration, the direction of insertion of the sheath introducer into a living body and the direction of insertion of the catheter into the sheath introducer can be made substantially opposite to each other.

[3] The direction changing device as above may further includes a holding section by which the first mounting section and the second mounting section are interconnected and their relative positions are held.

According to this configuration, the direction changing device includes the holding section by which relative positions of the first mounting section and the second mounting section are held, so that the first direction and the second direction can be suitably restrained from changing relatively.

[4] In the direction changing device as above, a configuration may be adopted wherein an intermediate section to which a shaft of the catheter or a sheath tube constituting the sheath introducer can be mounted constitutes a part or the whole part of the holding section, and a direction changing section including the first mounting section, the intermediate section, and the second mounting section is formed in a roughly U-shaped form in plan view.

According to this configuration, the catheter or sheath tube mounted to the direction changing section is also curved into a roughly U-shaped form in plan view. Therefore, the catheter can be inserted into the sheath tube comparatively easily.

[5] In the direction changing device as above, a configuration may be adopted wherein the direction changing section is formed with a receiving bore which opens at one end face and the other end face of the direction changing section and in which the shaft or the sheath tube can be disposed, and the direction changing section is formed in its outer circumferential surface with a slit which communicates with the receiving bore and which extends over the entire length of the direction changing section.

According to this configuration, by disposing the shaft of the catheter or the sheath tube in the disposing hole, the shape of the shaft or the sheath tube can be suitably made to correspond to the shape of the direction changing section. In addition, since the slit communicating with the receiving bore is formed over the whole length of the direction changing section, the shaft of the catheter or the sheath tube of the sheath introducer can be mounted into the receiving bore via the slit. This permits the shaft or the sheath tube to be easily mounted into the receiving bore. Besides, since mounting of the direction changing device to the sheath tube can be performed after the insertion of the sheath introducer into a living body, insertion of the sheath introducer into the living body can be carried out without being obstructed by the direction changing device.

[6] In the direction changing device as above, a configuration may be adopted wherein the direction changing section is flexible, and the slit is so formed that its width gradually decreases along the direction from the outer circumferential surface toward an inner circumferential surface of the direction changing section.

According to this configuration, the direction changing section is flexible, and the slit is so formed that its width gradually decreases along the direction from the outer circumferential surface toward the inner circumferential surface of the direction changing section. Therefore, for example by a process in which the shaft of the catheter or the sheath tube in the state of being located at the slit is pressed toward the receiving bore side, a wall part defining the slit of the direction changing section can be elastically deformed outward and the slit width can be thereby expanded. This permits the shaft or the sheath tube to be easily mounted into the receiving bore. Besides, since the wall part defining the slit returns into its original shape upon mounting of the shaft or the sheath tube into the receiving bore, the shaft or the sheath tube would not slip out via the slit.

[7] The direction changing device as above may further include a tapered section joined to one end of the first mounting section and formed therein with a hole which communicates with the receiving bore and decreases in diameter toward the receiving bore in a tapered manner.

According to this configuration, it is made easy to insert the shaft of the catheter or the sheath tube into the receiving bore through the tapered hole of the tapered section. Consequently, it is made easy to mount the shaft or the sheath tube into the receiving bore.

[8] In the direction changing device as above, a configuration may be adopted wherein the intermediate section and an interconnecting section interconnecting a lateral portion of the first mounting section and a lateral portion of the second mounting section constitute the whole part of the holding section, and the interconnecting section is formed with one or more than one joint section to which the direction changing section can be mounted on the other end side thereof.

According to this configuration, the direction changing section can be easily held in a roughly U-shaped form in plan view by the interconnecting section. In addition, since the direction changing section can be mounted to the joint section of the interconnecting section on the other end side thereof, the position at which the direction changing section is mounted to the joint section on the other end side thereof can be changed and, hence, the curvature of the direction changing section can be changed thereby. As a result, in the case of mounting the direction changing device to the shaft of a catheter, the frictional resistance generated between the catheter and the direction changing section can be adjusted according to the operator's preference. In the case of mounting the direction changing device to the sheath tube, the frictional resistance generated between the inside surface of the sheath tube and the catheter can be adjusted according to the operator's preference. Furthermore, where the interconnecting section is provided with a plurality of joint sections, the curvature of the direction changing section can be easily changed by changing the joint section to which the direction changing section is mounted on the other end side thereof.

[9] In the direction changing device as above, a configuration may be adopted wherein the first mounting section can be mounted to the catheter with the catheter in a slidable state, the second mounting section can be mounted to the sheath introducer, and in a condition where the catheter is slidably mounted to the first mounting section and the sheath introducer is mounted to the second mounting section, the catheter or the sheath introducer is put in a curved shape such that a first direction in which a catheter portion mounted to the first mounting section is followed along a distal direction of the catheter and a second direction in which a sheath introducer portion mounted to the second mounting section is followed along a distal direction of the sheath introducer are different from each other.

According to this configuration, the axial direction of the first mounting section and the axial direction of the second mounting section intersect each other or are parallel to each other in plan view, and, in the condition where the catheter is slidably mounted to the first mounting section and the sheath introducer is mounted to the second mounting section, the catheter or the sheath introducer is put in a curved shape such that the first direction and the second direction are different from each other. Therefore, the direction of insertion of the sheath introducer into a living body and the operating direction for the catheter can be easily set different from each other. This ensures that at the time of inserting the catheter into the sheath introducer, the catheter can be easily operated by the operator's dominant hand. Consequently, the catheter can be efficiently inserted into the living body.

[10] In the direction changing device, a configuration may be adopted wherein the sheath introducer has a sheath tube capable of being inserted into a living body, and a sheath hub connected to a proximal end of the sheath tube; the sheath hub is formed in its proximal end face with a catheter insertion port into which the catheter can be inserted; and the second mounting section is so formed that the sheath hub can be mounted thereto.

According to this configuration, the sheath hub formed with the catheter insertion port can be mounted to the second mounting section. Therefore, positional deviation of the catheter insertion port from the second mounting section can be suitably suppressed. As a result, the catheter can be easily inserted into the sheath introducer.

[11] In the direction changing device as above, a configuration may be adopted wherein a branch tube is connected to the sheath hub, the second mounting section is formed with a receiving bore in which the sheath hub can be disposed, and a wall part defining the receiving bore is formed with a cutout in which the branch tube can be disposed.

According to this configuration, it is ensured that even where the branch tube is connected to the sheath hub, the branch tube can be disposed in the cutout. Therefore, the sheath hub can be mounted into the receiving bore in the second mounting section, while preventing interference between the branch tube and the second mounting section.

[12] In the direction changing device as above, a configuration may be adopted wherein in a condition where the catheter is slidably mounted to the first mounting section and the sheath introducer is mounted to the second mounting section, the catheter or the sheath introducer is put in a curved shape such that the first direction and the second direction are substantially opposite to each other.

According to this configuration, the direction of insertion of the sheath introducer into a living body and the operating direction for the catheter can be set substantially opposite to each other.

[13] The direction changing device as above may further include a holding section by which the first mounting section and the second mounting section are interconnected and their relative positions are held.

According to this configuration, the direction changing device has the holding section by which relative positions of the first mounting section and the second mounting section are held. Therefore, the first direction and the second direction can be suitably restrained from changing relatively.

[14] In the direction changing device as above, a configuration may be adopted wherein an intermediate section which guides the catheter from the first mounting section to the second mounting section constitutes a part or the whole part of the holding section, and a direction changing section including the first mounting section, the intermediate section, and the second mounting section is formed in a roughly U-shaped form in plan view.

According to this configuration, the catheter can be guided from the first mounting section to the second mounting section by the intermediate section. Therefore, the catheter can be inserted into the sheath introducer more easily. In addition, since the direction changing section is formed in a roughly U-shaped form in plan view, the catheter mounted into the direction changing section is also curved into a roughly U-shaped form in plan view. Therefore, the catheter can be inserted into the sheath introducer comparatively smoothly.

[15] In the direction changing device as above, a configuration may be adopted wherein the holding section is formed with the second mounting section defining a disposing hole in which the sheath hub can be disposed, and an introduction hole which communicates with the receiving bore and in which the catheter is slidable; and the catheter insertion port and the introduction hole communicate with each other in a condition where the sheath hub is disposed in the receiving bore.

According to this configuration, the holding section is formed with the second mounting section defining the receiving bore and with the introduction hole, and the catheter insertion port and the introduction hole communicate with each other in the condition where the sheath hub is disposed in the receiving bore. Therefore, the catheter can be assuredly introduced into the catheter insertion port of the sheath hub, with a simple configuration.

[16] A medical apparatus assembly including: a catheter; a sheath introducer having a sheath tube insertable into a living body and a sheath hub provided at a proximal end of the sheath tube; and a direction changing device to be mounted to the catheter or the sheath introducer, wherein the direction changing device is the direction changing device as described above.

According to the medical apparatus assembly configured as above, the same effects as those of the above-described direction changing device can be obtained.

As above-described, according to embodiments of the present invention, the axial direction of the first mounting section and the axial direction of the second mounting section intersect each other or are parallel to each other in plan view, and, in the condition where a catheter or a sheath introducer is mounted to the first mounting section and the second mounting section, the catheter or the sheath introducer can be put in a curved shape such that the first direction and the second direction are different from each other. Therefore, it is ensured that at the time of inserting the catheter into the sheath introducer, the catheter can be easily operated by the operator's dominant hand. Consequently, the catheter can be inserted into the living body in an efficient manner.

BRIEF DESCRIPTION OF THE DRAWINGS

FIG. 16 is a schematic plan view of a medical assembly having a direction changing device according to a second embodiment of the present invention;

DETAILED DESCRIPTION OF THE PREFERRED EMBODIMENTS

Figure 1:
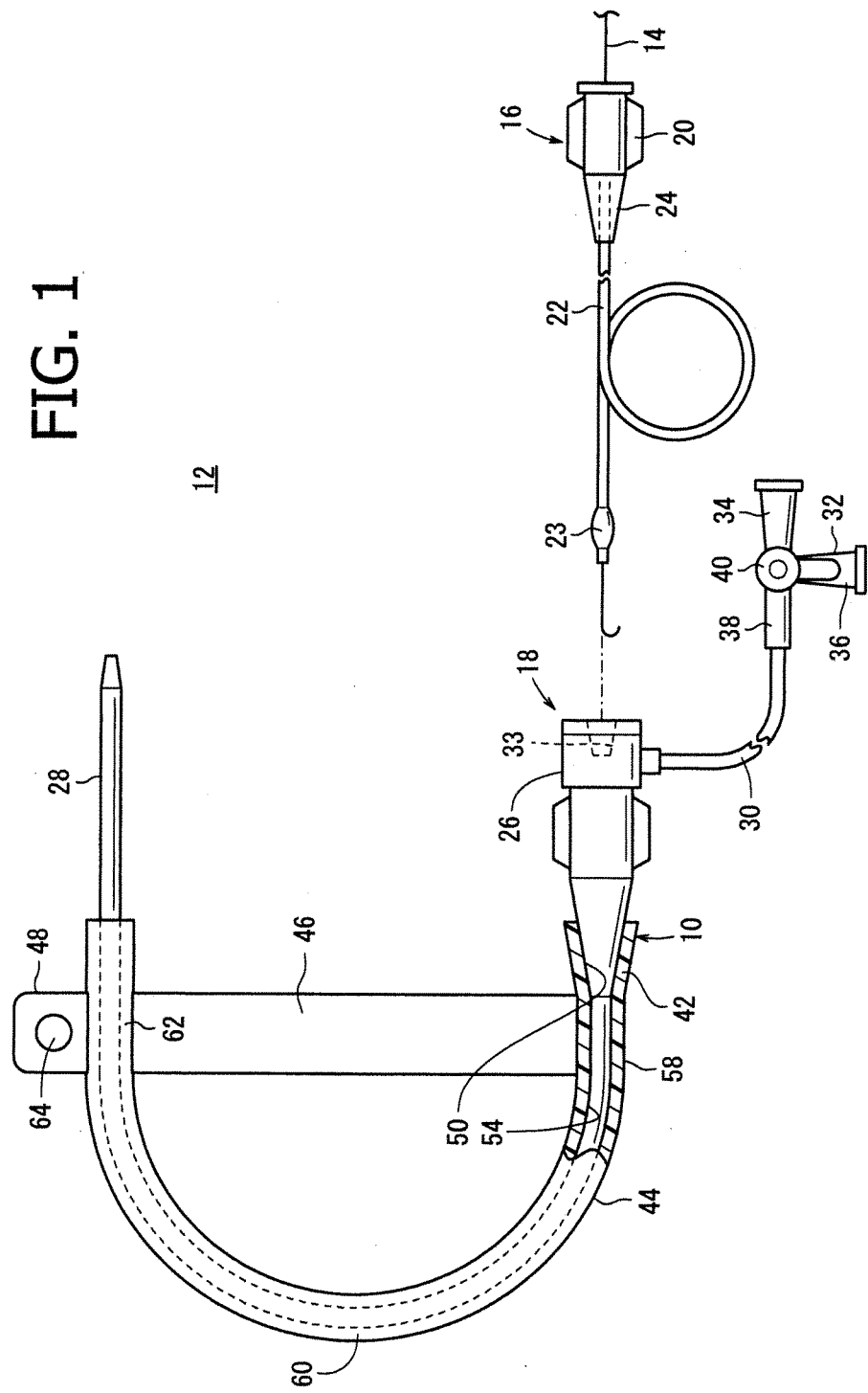
FIG. 1 is a schematic plan view of a medical assembly having a direction changing device according to a first embodiment of the present invention.

A direction changing device and a medical assembly having the same according to the present invention will be described in detail below, by showing preferred embodiments thereof and referring to the accompanying drawings.
First Embodiment As shown in FIG. 1, a medical assembly 12 has a guidewire 14, a catheter 16, a sheath introducer 18, and a direction changing device 10. Incidentally, the sheath introducer 18 includes not only a sheath but also a long sheath and a guiding sheath.

The guidewire 14 is a member which is inserted in a lumen of the catheter 16 and by which the catheter 16 is guided in an organ of a living body such as a blood vessel to a predetermined target site therein. A distal portion of the guidewire 14 has been set, for example, into a roughly J-shaped form. Examples of the material forming the guidewire 14 include a polyurethane resin and stainless steel. The shape of the distal portion of the guidewire 14 is not limited to the above-mentioned shape but may be others such as a straight shape, an angular shape or the like.

The catheter 16 is configured to be percutaneously inserted into an organ of a living body, such as a blood vessel, for diagnosis or treatment of a part thereof having a lesion (e.g., stenosed part) of the living body organ. The catheter 16 may be configured as a guiding catheter, a balloon catheter or the like. In this embodiment, the catheter 16 is configured as a balloon catheter.

The catheter 16 has a catheter hub 20, a small-diameter long shaft 22 connected to the distal end of the catheter hub 20, and an anti-kinking protector 24 which is provided at the distal end of the catheter hub 20 and surrounds a proximal side of the shaft 22.

The catheter hub 20 is a hollow member which holds the proximal portion of the shaft 22 at the distal end thereof, and is formed, for example, from a hard resin such as polycarbonate.

The shaft 22 is formed in a hollow shape (hollow cylindrical shape), from a resin or the like having adequate flexibility and adequate strength so that it can be smoothly advanced inside an organ of a living body while the operator grips and operates the proximal side thereof. The lumen of the shaft 22 communicates with the lumen of the catheter hub 20. A distal portion of the shaft 22 is provided with an inflatable balloon part 23. In FIG. 1, the balloon part 23 is shown in an inflated state. The balloon part 23 is used in such an inflated state, after reaching a target site in a living body through the sheath introducer 18 and the like.

The anti-kinking protector 24 is operable to prevent kinking from occurring at that portion of the shaft 22 which is joined to the catheter hub 20. For instance, the anti-kinking protector 24 is a member which is formed in a tapered tubular shape from a resin having adequate flexibility and rigidity for its anti-kinking function.

The sheath introducer 18 is configured for smooth insertion of the shaft 22 of the catheter 16 into a blood vessel, for example. The sheath introducer 18 includes a sheath hub 26, a sheath tube 28 connected to a distal end of the sheath hub 26, a branch tube 30 connected to a lateral portion of the sheath hub 26, and a three-way cock 32 provided on the branch tube 30.

The sheath hub 26 is a hollow member formed from a resin or the like, and has an opening at its proximal end face forming a catheter insertion port 33 into and through which the shaft 22 of the catheter 16 can be inserted. In the lumen at the proximal side in the sheath hub 26 is a valve element (check valve) (not shown) for preventing liquid such as blood from leaking out therefrom. The valve element is composed of an elastic member of silicone rubber or the like which is formed with a predetermined slit and in which the shaft 22 of the catheter 16 can be inserted. A distal portion of the sheath hub 26 tapers down in a distal direction.

The sheath tube 28 is formed from a flexible material, and has a lumen with a substantially constant inside diameter along the axial direction thereof. The lumen of the sheath tube 28, communicating with the lumen of the sheath hub 26, is sized so that the shaft 22 of the catheter 16 can be inserted therein and passed therethrough. The distal end of the sheath tube 28 tapers down in a distal direction.

The branch tube 30 is formed from a flexible material, and is connected to a lateral side of a proximal portion of the sheath hub 26 at a distal position relative to the valve element. The lumen of the branch tube 30 communicates with the lumen of the sheath hub 26.

The three-way cock 32 is provided at an end portion of the branch tube 30, opposite to the end connected to the sheath hub 26. The three-way cock 32 includes an air discharge port 34, a medicinal liquid (e.g., heparin-added physiological saline) injection port 36 to which a syringe (not shown) or the like is connected, a port 38 for connection to the end portion of the branch tube 30, and a cock 40 for switching the communication conditions of these ports 34, 36, 38. In this embodiment, naturally, the port 34 may be used as a medicinal liquid injection port, and the port 36 as an air discharge port.

The direction changing device 10 is to be mounted to the sheath introducer 18, and is integrally formed from a flexible material (resin or the like).

Figure 2:
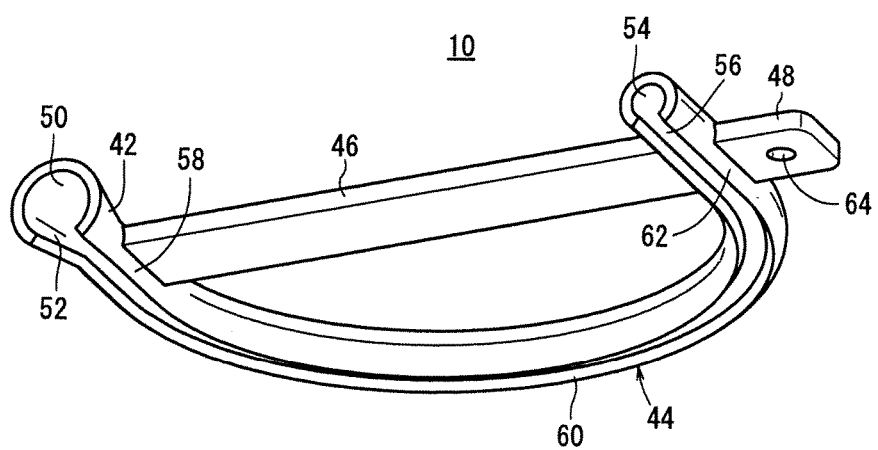
FIG. 2 is a perspective view of the direction changing device.
Figure 3:
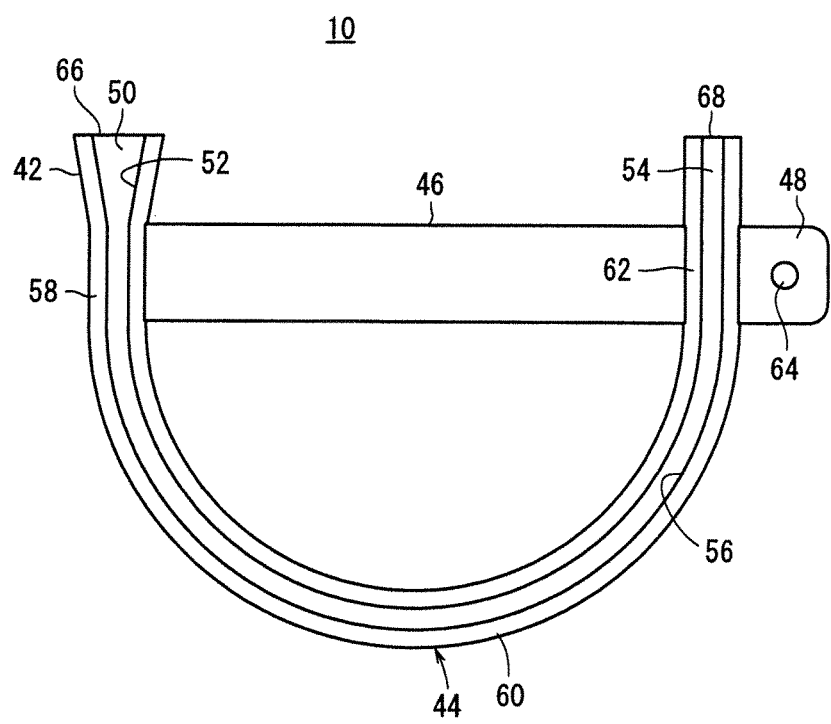
FIG. 3 is a plan view of the direction changing device.
Figure 4:
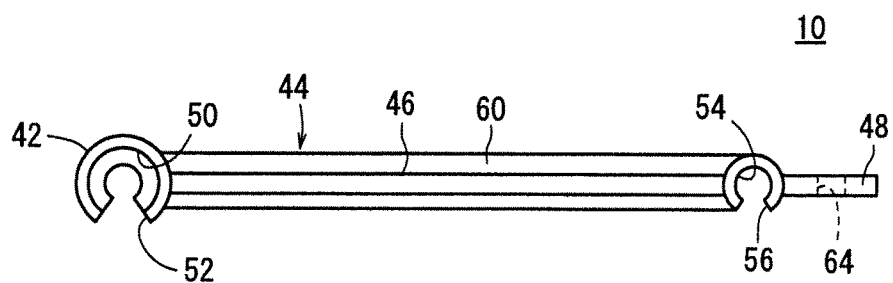
FIG. 4 is a front elevational view of the direction changing device.

As shown in FIGS. 2 to 4, the direction changing device 10 includes a tapered section 42, a direction changing section 44 formed to be continuous with the tapered section 42 and roughly U-shaped in plan view, a plate-shaped interconnecting section 46 provided on the direction changing section 44, and a plate-shaped locking section 48 for locking the direction changing section 44 to a patient 106 (see FIG. 5) or the like.

The tapered section 42 is formed with a first receiving bore 50 whose diameter gradually decreases toward the direction changing section 44 in a tapered manner. An inner circumferential surface of the tapered section 42 (a wall surface defining the first receiving bore 50) can be contacted by a distal portion of the sheath hub 26 of the sheath introducer 18 (see FIG. 1).

The tapered section 42 has a first slit 52 formed in its outer circumferential surface that extends through tapered, annular wall of the tapered section 42 to communicate with the first receiving bore 50, over the entire axial length of the tapered section 42. The first slit 52 gradually narrows in width as it extends axially toward the direction changing section 44 (see FIG. 3). In addition, the first slit 52 gradually narrows in width as it extends radially toward the first receiving bore 50 (see FIG. 4). In other words, the first slit 52 is formed to gradually decrease in width as it extends along the radial direction from the outer circumferential surface toward the inner circumferential surface (the wall surface defining the first receiving bore 50) of the tapered, annular wall of section 42. Alternatively, the tapered section 42 may have a constant diameter. Further, the first slit 52 may have a constant width, without any narrowing thereof.

The direction changing section 44 is formed with a tubular shape, and has a lumen (second receiving bore 54) with a constant inside diameter in which the sheath tube 28 of the sheath introducer 18 can be disposed. The second receiving bore 54 communicates with the first receiving bore 50. In other words, the first receiving bore 50 and the second receiving bore 54 together form a single receiving bore. The inside diameter of the second receiving bore 54 is sized that the sheath tube 28 can be inserted therein (passed therethrough).

The direction changing section 44 has a second slit 56 formed in its outer circumferential surface, which extends through the annular wall of the section 44 to communicate with the second receiving bore 54. The slit 56 has a constant width and over the entire length of the direction changing section 44 (see FIG. 3). The second slit 56 gradually narrows in width as it extends toward the second receiving bore 54 (see FIG. 4). In other words, the second slit 56 is formed to gradually decrease in width as it extends in the radial direction from the outer circumferential surface toward the inner circumferential surface (the wall surface defining the second receiving bore 54) of the direction changing section 44. The second slit 56 communicates with the first slit 52. Thus, the first slit 52 and the second slit 56 together form a single slit.

The direction changing section 44 includes a first mounting section 58 at one end portion of the direction changing section 44 and which is continuous with the distal end of the tapered section 42, an intermediate section 60 continuous with the first mounting section 58, and a second mounting section 62 at the other end portion of the direction changing section 44 and which is continuous with the intermediate section 60.

The interconnecting section 46 interconnects one end portion and the other end portion of the direction changing section 44. That is, the interconnecting section 46 interconnects the first mounting section 58 and the second mounting section 62. This ensures that the shape of the direction changing section 44 can be held and retained in a roughly U-shaped form in plan view. The locking section 48 is adjacent to the interconnecting section 46, with the direction changing section 44 extending therebetween. The locking section 48 has a hole 64 formed generally centrally therein and through which a suture can be inserted.

In the direction changing device 10 configured as described above, the axial direction of the first mounting section 58 (the extending direction of the second receiving bore 54 in the first mounting section 58) and the axial direction of the second mounting section 62 (the extending direction of the second receiving bore 54 in the second mounting section 62) are parallel to each other in plan view.

When the sheath tube 28 is mounted to the direction changing section 44, the sheath tube portion mounted to the first mounting section 58 extends proximally to distally in one direction (the first direction; the leftward direction in FIG. 1), and the sheath tube portion mounted to the second mounting section 62 extends proximally to distally in another direction (the second direction; the rightward direction in FIG. 1) with the directions generally being opposite to each other.

In addition, the intermediate section 60 and the interconnecting section 46 function as a holding section which interconnects the first mounting section 58 and the second mounting section 62 and holds the positions of these mounting sections 58, 62 stationary relative to each other. This makes it possible to suitably restrain the first direction and the second direction from changing relative to each other.

Further, an aperture (first aperture 66) that opens at one end face of the tapered section 42 and an aperture (second aperture 68) that opens at the other end face of the direction changing section 44 (the other end face of the second mounting section 62) are not oriented to face opposite to each other but are oriented to face in substantially the same direction.

Operation of the medical assembly 12 configured as above will be described below.

Figure 5:
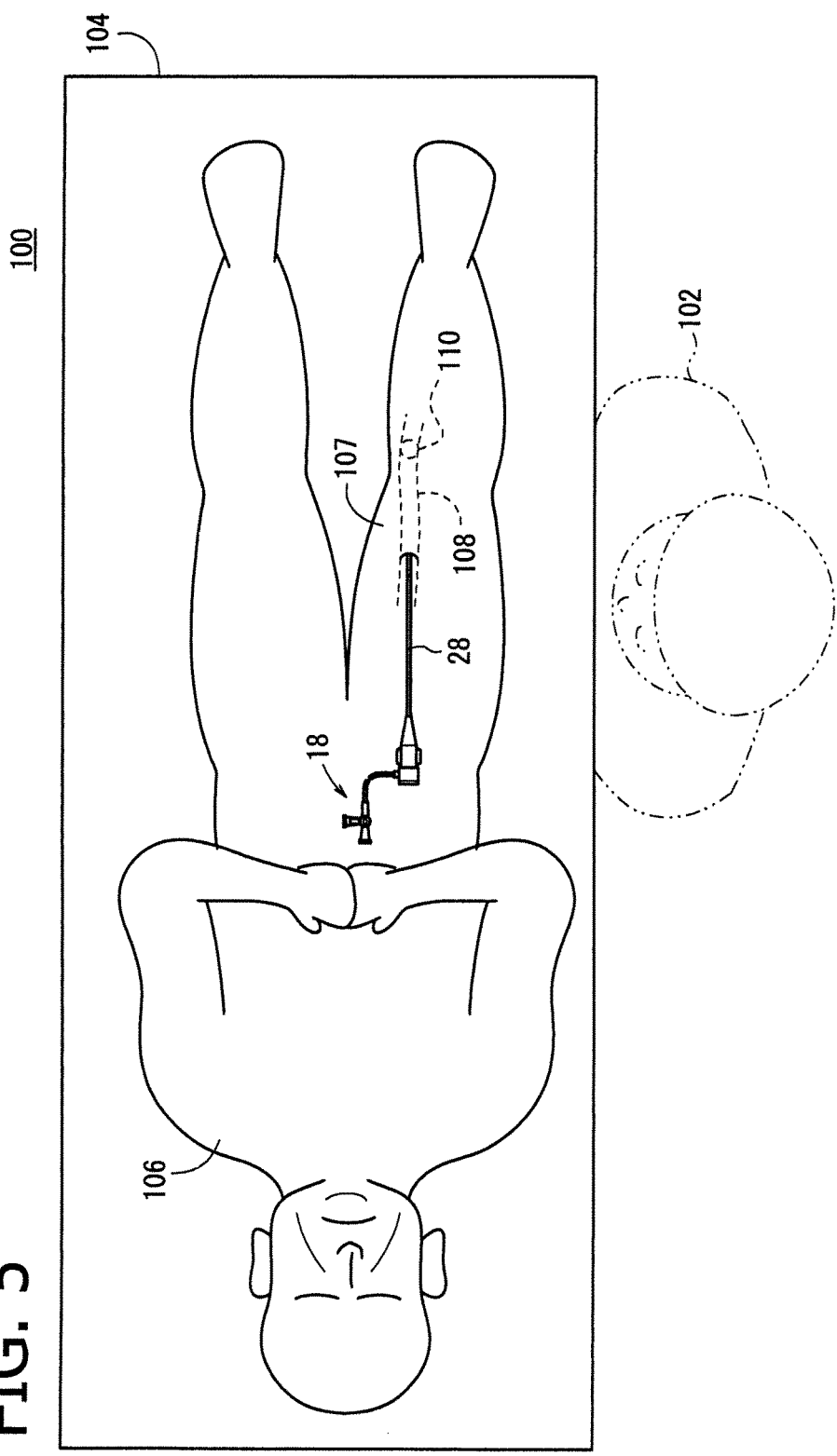
FIG. 5 is an illustration of a condition where a sheath introducer is indwelling in a femoral region of the right leg of a patient lying supine on an operating table.

As shown in FIG. 5, in an operating room 100, an operator 102 commonly performs an operation while being located on the right side of a patient 106 lying supine on an operating table 104. In the following description, the "right side"

means the right side (the right side in FIG. 5) of the operator 102 facing the patient 106, and the "left side" means the left side (the left side in FIG. 5) of the operator 102 facing the patient 106.

In this embodiment, an example will be described in which the catheter (balloon catheter) 16 constituting the medical apparatus assembly 12 is inserted into the superficial femoral artery 108 of the right leg 107 of the patient 106 and a lesion (stenosed part) 110 located on the foot side of the patient 106 is treated.

Figure 6:
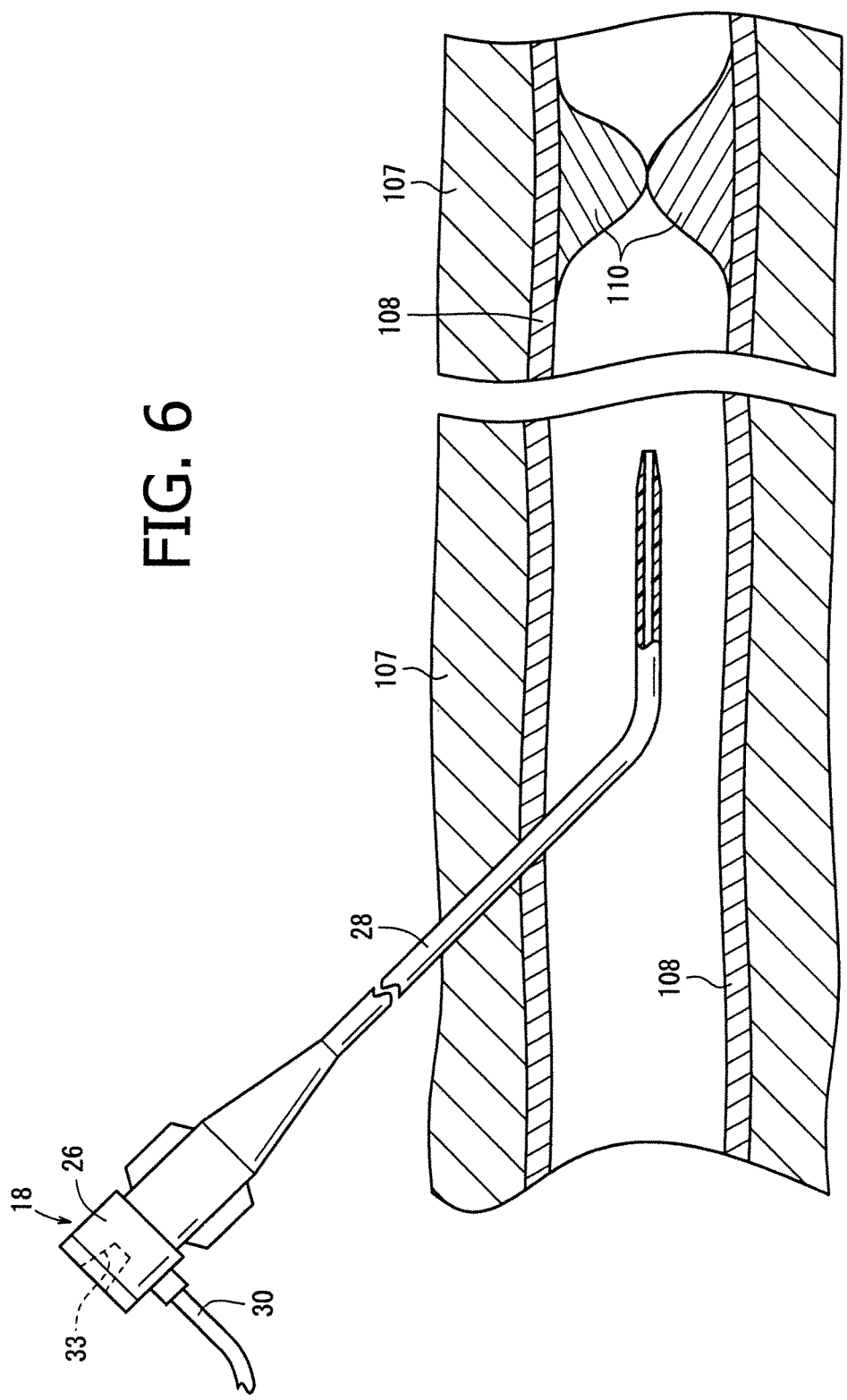
FIG. 6 is an illustration of a condition where the sheath introducer is inserted in a superficial femoral artery.

First, the operator 102, in the state of standing at the right side of the patient 106 lying supine on the operating table 104 in the operating room 100, inserts the sheath tube 28 of the sheath introducer 18 into the superficial femoral artery 108 of the right leg 107 of the patient 106, by a sheath method, for example (see FIG. 6).

In this instance, the lesion 110 is located on the foot side relative to the superficial femoral artery 108. Therefore, the operator 102 inserts the sheath tube 28 into the right leg 107 (into the living body) so that the sheath tube 28 is oriented toward the right side. Consequently, in the condition where the sheath tube 28 is placed in the right leg 107, the catheter insertion port 33 of the sheath hub 26 is oriented so that it opens and faces toward the left side (in FIG. 6, toward a left upper side).

According to the conventional method, it has been a common practice, in this condition, to insert the shaft 22 of the catheter 16 into the sheath introducer 18. In that case, the operator 102 may be forced to perform the required operation with their left hand to insert the shaft 22 of the catheter 16 into the sheath introducer 18, so that the shaft 22 can be advanced toward the right side. Therefore, when the operator 102 is right-handed, the catheter 16 is manipulated by their left hand which is not the operator's dominant hand. Consequently, the operator 102 may fail to smoothly insert the shaft 22 of the catheter 16 into the sheath introducer 18.

Figure 7:
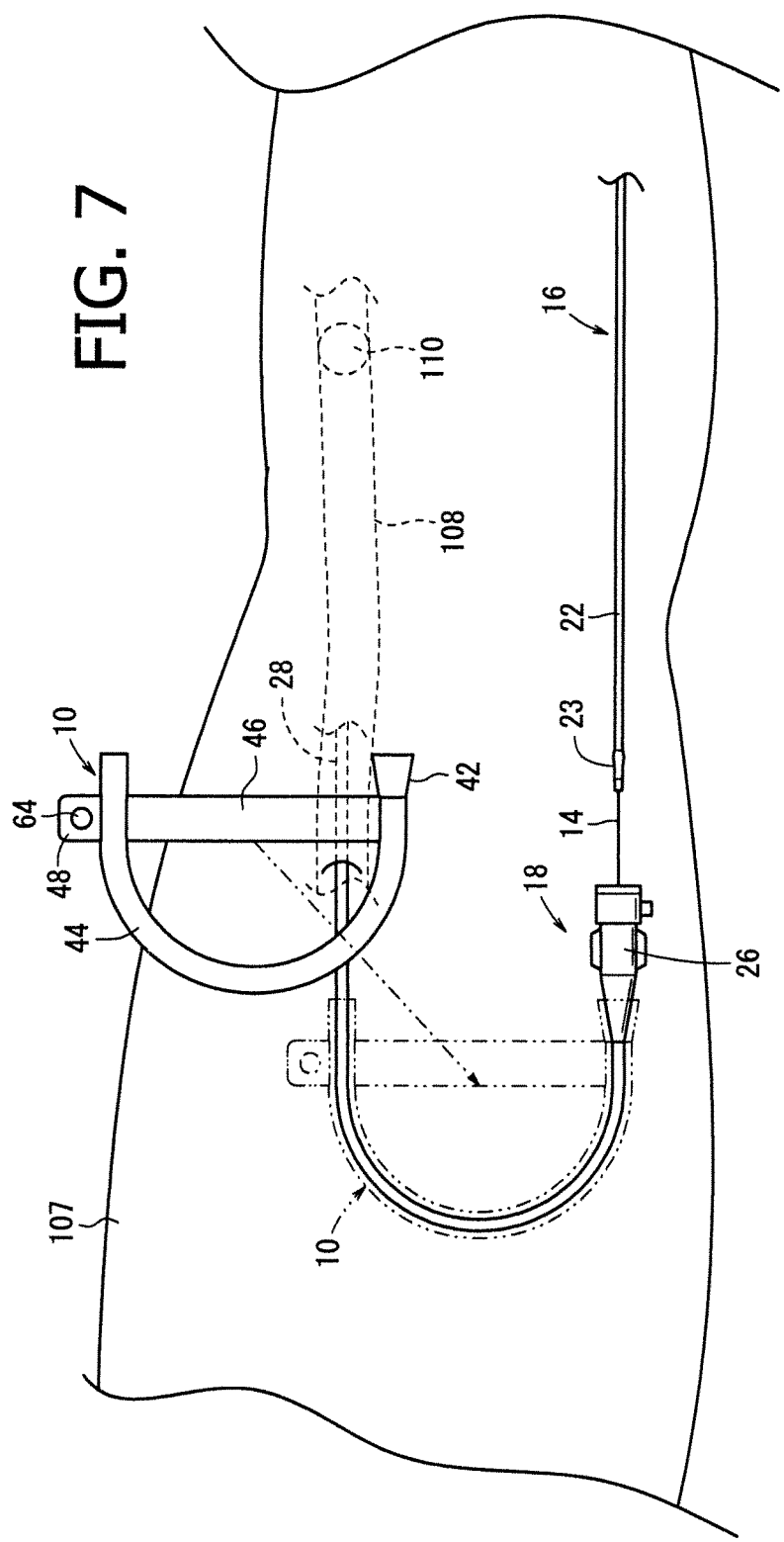
FIG. 7 is an illustration of the mounting of the direction changing device to the sheath introducer.

To cope with this problem, in this embodiment, after the sheath tube 28 is placed in the right leg 107, the operator 102 mounts the direction changing device 10 to the sheath introducer 18 (see FIG. 7). Specifically, a distal portion of the sheath hub 26 is mounted into the first receiving bore 50 via the first slit 52 of the direction changing device 10, and the sheath tube 28 is mounted into the second receiving bore 54 via the second slit 56 of the direction changing device 10 while curving the sheath tube 28 into a roughly U-shaped form.

In this embodiment, the direction changing device 10 is flexible, and the first slit 52 is formed to gradually decrease in width along the radial direction from the outer circumferential surface toward the inner circumferential surface of the tapered section 42. Therefore, for example when a distal portion of the sheath hub 26 adjacent the first slit 52 is pressed inwardly toward the first receiving bore 50, the wall portions defining the first slit 52 can be elastically deformed outwardly and the slit width can be thereby expanded. This ensures easy mounting of the distal portion of the sheath hub 26 into the first receiving bore 50. After the distal portion of the sheath hub 26 is thus mounted in the first receiving bore 50, the wall portions defining the first slit 52 return to their original shape to provide a snap-fit connection of the sheath hub 26 in the bore 50. As a result, the distal portion of the sheath hub 26 will not slip out of the bore 50 via the first slit 52.

Similarly, in this embodiment, the second slit 56 is formed to gradually decrease in width along the radial direction from the outer circumferential surface toward the inner circumferential surface of the direction changing section 44. Therefore, for example when the sheath tube 28 adjacent the second slit 56 is pressed inwardly toward the second receiving bore 54 side, the wall portions defining the second slit 56 can be elastically deformed outwardly and the slit width can be thereby expanded. This ensures easy mounting of the sheath tube 28 into the second receiving bore 54. After the sheath tube 28 is mounted to the second receiving bore 54, the wall portions defining the second slit 56 returns to their original shape to provide a snap-fit connection of the sheath tube 28 in the bore 54. Consequently, the sheath tube 28 will not slip out of the bore 54 via the second slit 56.

Figure 8:
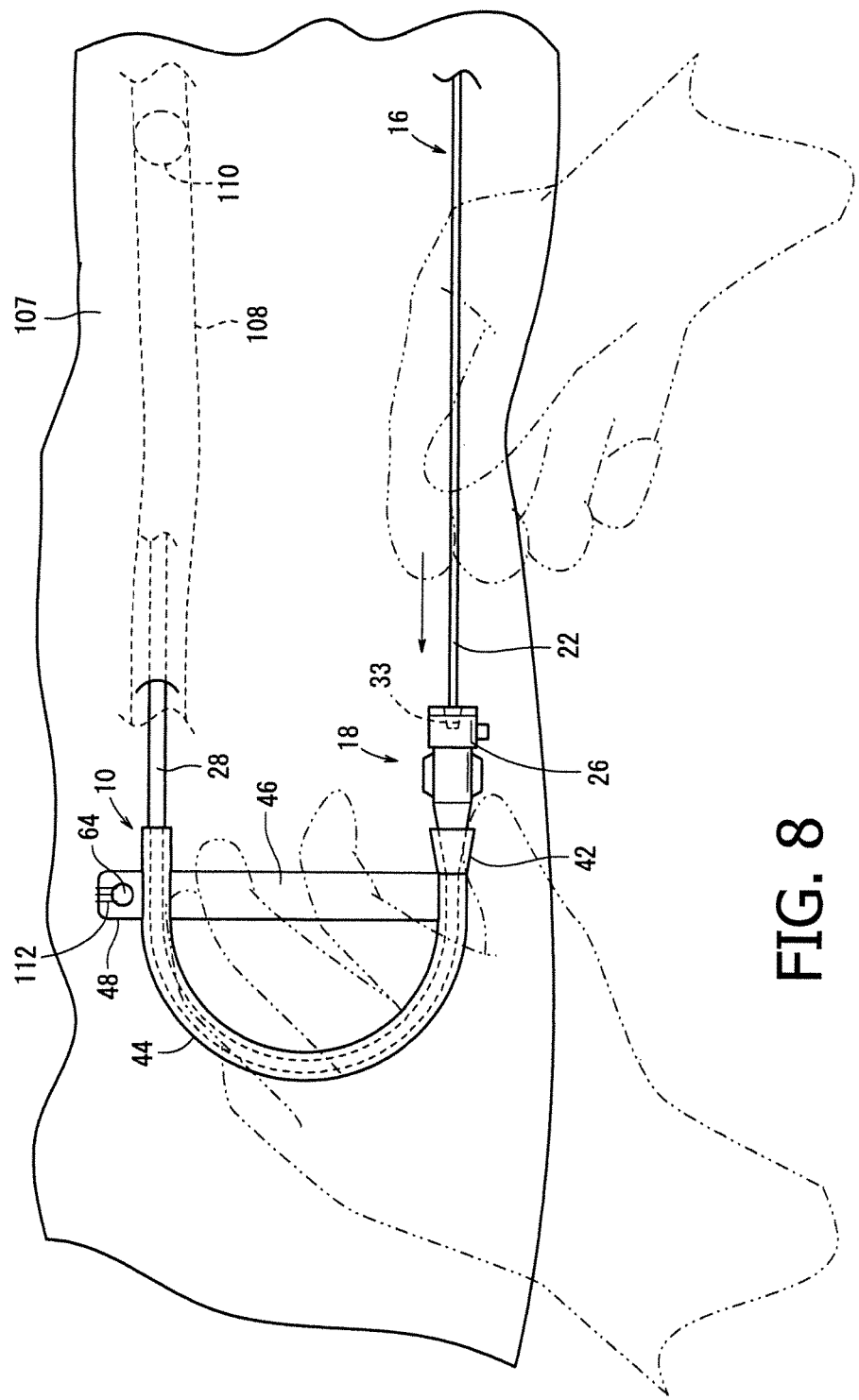
FIG. 8 is an illustration of a shaft of a catheter being inserted in a sheath introducer which is mounted in first and second receiving bores of the direction changing device.

Subsequently, the operator 102 sutures the locking section 48 of the direction changing device 10 to the skin of the patient 106 to each other with a suture 112 (see FIG. 8). This results in securing or locking the direction changing device 10 to the patient 106. Incidentally, the locking section 48 may be sutured to a cover body covering the patient 106, instead of the skin of the patient 106. The cover body covering the patient 106 may be a drape, for example. Alternatively, the locking section 48 may be held in position with a tape or the like, or may be fixedly adhered to the patient or the drape. The locking section 48 may not necessarily be located in the region shown. For example, the locking section 48 may be disposed on the opposite side of the interconnecting section 46 or may be disposed at an intermediate part of the interconnecting section 46. The number of the locking section(s) 48 is not limited to one, and may be two or more.

In this condition, the catheter insertion port 33 of the sheath hub 26 is oriented so that it opens and faces toward the right side. In other words, the direction of insertion of the sheath tube 28 into the right leg 107 and the direction of insertion of the shaft 22 of the catheter 16 into the sheath introducer 18 are substantially opposite to each other. Specifically, the direction of insertion of the sheath tube 28 into the right leg 107 is rightward, whereas the direction of insertion of the shaft 22 of the catheter 16 into the sheath introducer 18 is leftward.

Figure 9:
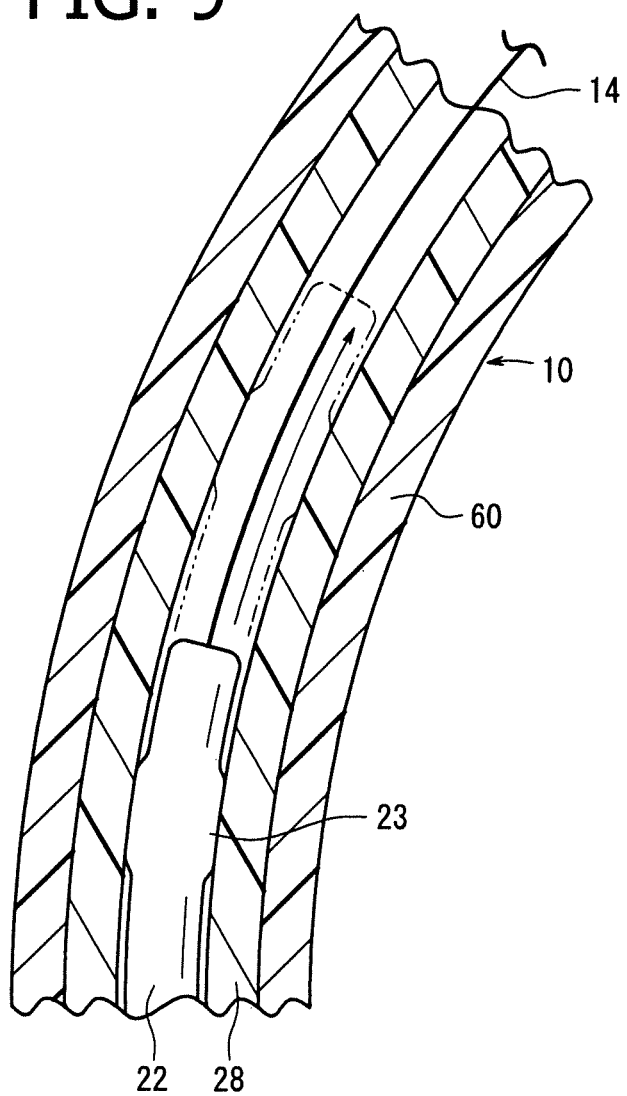
FIG. 9 is a fragmentary sectional illustration of the shaft of the catheter being passed through a sheath tube of the sheath introducer.
Figure 10:
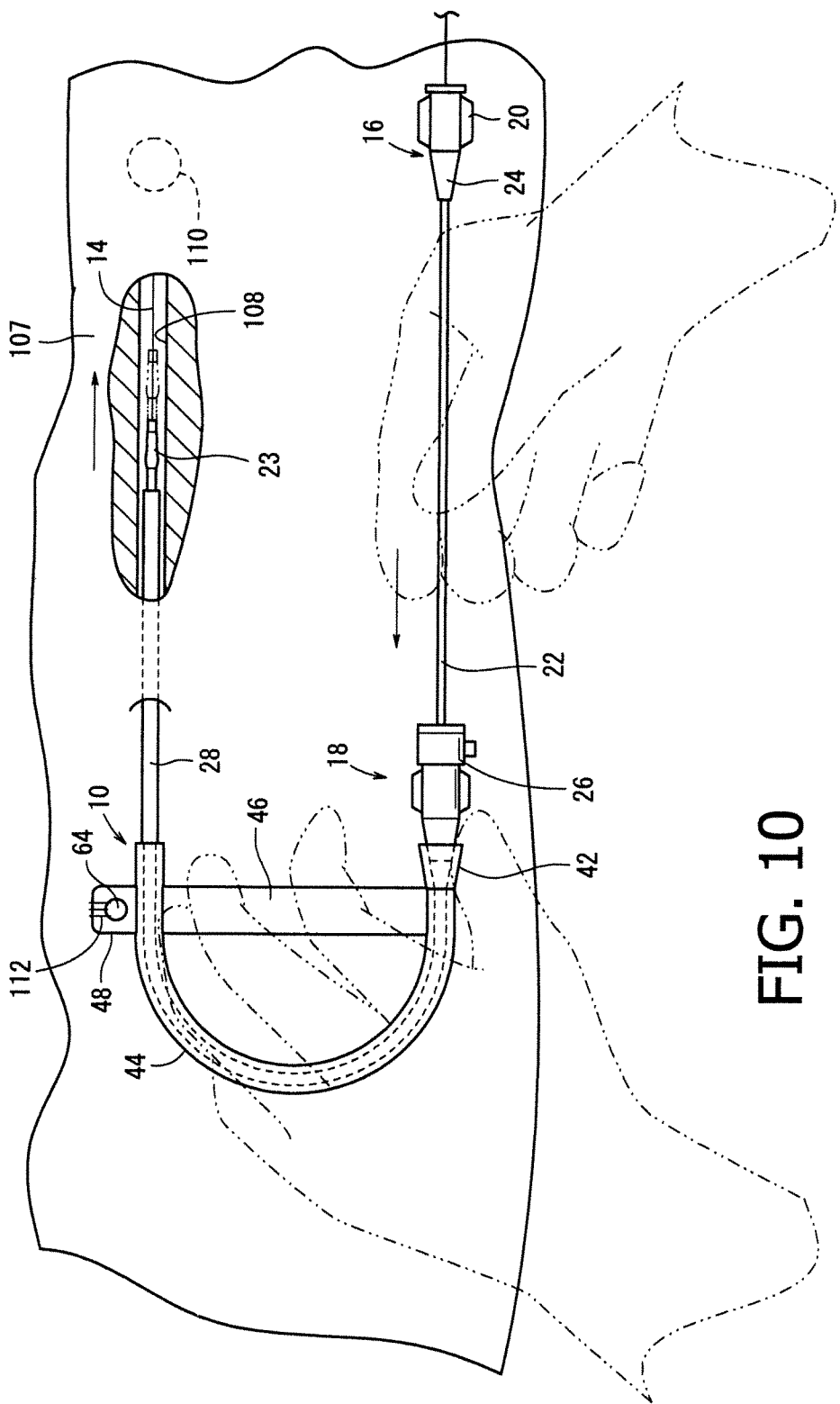
FIG. 10 is an illustration of the shaft of the catheter being inserted into the sheath introducer to thereby advance the shaft within the superficial femoral artery.

This permits the operator 102 to easily insert the shaft 22 of the catheter 16 into the catheter insertion port 33 of the sheath hub 26 while operating the catheter 16 with their right hand, namely, the dominant hand of the operator 102. Then, the shaft 22 of the catheter 16 thus inserted into the lumen of the sheath hub 26 is passed through the curved lumen of the sheath tube 28 (see FIG. 9), and inserted into the superficial femoral artery 108 (FIG. 10).

Thereafter, the operator 102 delivers the balloon part 23 of the shaft 22 of the catheter 16 to the lesion 110, and inflates the balloon part 23, thereby treating the lesion 110.

According to this embodiment, in the condition where the axial direction of the first mounting section 58 and the axial direction of the second mounting section 62 are parallel to each other in plan view and where the sheath tube 28 is mounted to the direction changing section 44, the sheath tube 28 is held in a curved shape such that the sheath tube portion mounted to the first mounting section 58 extends proximally to distally in one direction and the sheath tube portion mounted to the second mounting section 62 extends proximally to distally in another direction with these directions being opposite to each other. Therefore, the direction of insertion of the sheath tube 28 into the right leg 107 and the direction of insertion of the catheter 16 into the sheath introducer 18 can be set to be substantially opposite to each other. This ensures that at the time of inserting the catheter 16 into the sheath introducer 18, the catheter 16 can be easily operated by the operator's dominant hand. Consequently, the catheter 16 can be efficiently inserted into the living body.

In addition, since the direction changing section 44 is formed in a roughly U-shaped form in plan view, the sheath tube 28 mounted into the second receiving bore 54 of the direction changing section 44 can also be curved into a roughly U-shaped form in plan view. This permits the shaft 22 of the catheter 16 to be inserted into the sheath tube 28 comparatively smoothly.

Further, the tapered section 42 is formed with the first receiving bore 50, and the direction changing section 44 is formed with the second receiving bore 54 which communicates with the first receiving bore 50. By disposing the distal portion of the sheath hub 26 in the first receiving bore 50 and disposing the sheath tube 28 in the second receiving bore 54, therefore, it is possible to mount the sheath introducer 18 to the direction changing device 10 in a secure manner.

According to this embodiment, the first slit 52 communicating with the first receiving bore 50 is formed along the entire length of the tapered section 42, and the second slit 56 communicating with the second receiving bore 54 is formed along the entire length of the direction changing section 44. Therefore, the sheath hub 26 can be mounted into the first receiving bore 50 through the first slit 52, and the sheath tube 28 can be mounted into the second receiving bore 54 via the second slit 56. This enables easy mounting of the direction changing device 10 to the sheath introducer 18. Furthermore, the mounting of the direction changing device 10 to the sheath tube 28 can be carried out after the distal portion of the sheath tube 28 is inserted into the right leg 107 of the patient 106. This ensures that at the time of inserting the distal portion of the sheath tube 28 into the right leg 107, the direction changing device 10 would not obstruct the inserting operation.

In this embodiment, the sheath hub 26 can make contact with the wall surface defining the first receiving bore 50, so that the sheath hub 26 can be positioned relative to the direction changing device 10 and held in situ. This enables easy insertion of the shaft 22 of the catheter 16 into the catheter insertion port 33 of the sheath hub 26.

In addition, the locking section 48 is locked to the patient 106 by suturing the locking section 48 and the skin of the patient 106 to each other with the suture 112. This ensures that at the time of inserting the shaft 22 of the catheter 16 into the sheath introducer 18, the sheath tube 28 can be suitably inhibited from slipping out of the right leg 107.

In the medical assembly 12 according to this embodiment, as shown in FIG. 1, the direction changing device 10 may be preliminarily mounted to the sheath introducer 18 prior to insertion of the sheath tube 28 into the patient's body, such as into their leg 107. In this case, the direction changing device 10 may be mounted to the sheath introducer 18 by inserting the sheath tube 28 via the first aperture 66, and advancing it through the first receiving bore 50 and the second receiving bore 54, to reach the second aperture 68. In this instance, since the first receiving bore 50 increases in diameter toward the first aperture 66 in a tapered manner (decreases in diameter toward the direction changing section 44 in a tapered manner), the distal end of the sheath tube 28 can be easily inserted into the first aperture 66.

This embodiment is not restricted to the above-described configuration. For instance, in the direction changing device 10 according to this embodiment, the interconnecting section 46 may be omitted. In this case, the intermediate section 60 alone constitutes the holding section by which the first mounting section 58 and the second mounting section 62 are interconnected and their positions are fixed relative to each other. In such a configuration, also, the direction changing section 44 can be held or fixed in a roughly U-shaped form in plan view.

The direction changing device 10 according to this embodiment is not restricted to the example in which it is mounted to the sheath tube 28 of the sheath introducer 18. For instance, the direction changing device 10 may be mounted to (engaged with) the shaft 22 of the catheter 16 in such a manner that the shaft 22 is slidable therein.

Figure 11:
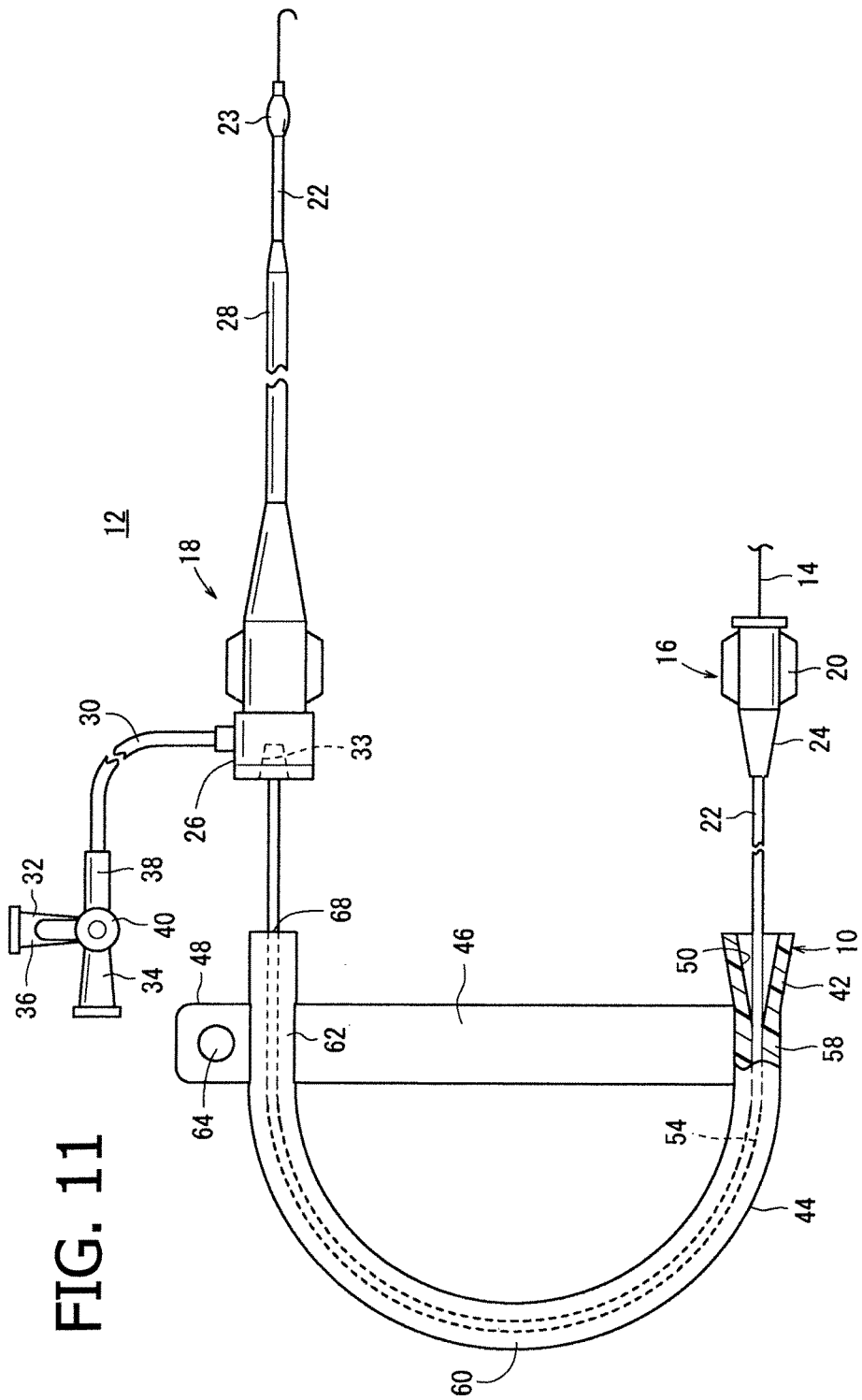
FIG. 11 is a schematic plan view of the medical assembly for illustrating an example in which the direction changing device shown in FIG. 1 is mounted to a shaft of a catheter.

Specifically, as shown in FIG. 11, for example the direction changing device 10 may be arranged such that the catheter insertion port 33 of the sheath introducer 18 and the aperture (second aperture 68) of the second receiving bore 54 at the end of the direction changing device 10 face each other; in this state, the shaft 22 of the catheter 16 may be advanced and passed through the first receiving bore 50 and the second receiving bore 54 of the direction changing device 10, to be inserted into the catheter insertion port 33.

In other words, when the shaft 22 of the catheter 16 is inserted into the first receiving bore 50 and the second receiving bore 54 of the direction changing device 10, the shaft 22 is forced to curve in a roughly U-shaped form in plan view, whereby the advancing direction of the shaft 22 is changed or redirected by about 180 degrees. Even where the catheter insertion port 33 is oriented to face leftward, therefore, the operator 102 can easily insert the shaft 22 into the sheath introducer 18 by operating the catheter 16 with their right hand, which is usually the operator's dominant hand. In this case, the second receiving bore 54 of the direction changing device 10 can be so formed that its inside diameter corresponds to the outside diameter of the shaft 22.

First Modification of First Embodiment

A direction changing device 10a according to a first modification of this embodiment will be described below, referring to FIGS. 12A and 12B. Incidentally, in the direction changing device 10a according to this modification, the same components as those of the above-described direction changing device 10 are denoted by the same reference symbols as used above, and detailed descriptions of them will be omitted. The same applies also to direction changing device 10c according to a third modification which will be described later.

Figure 12A:
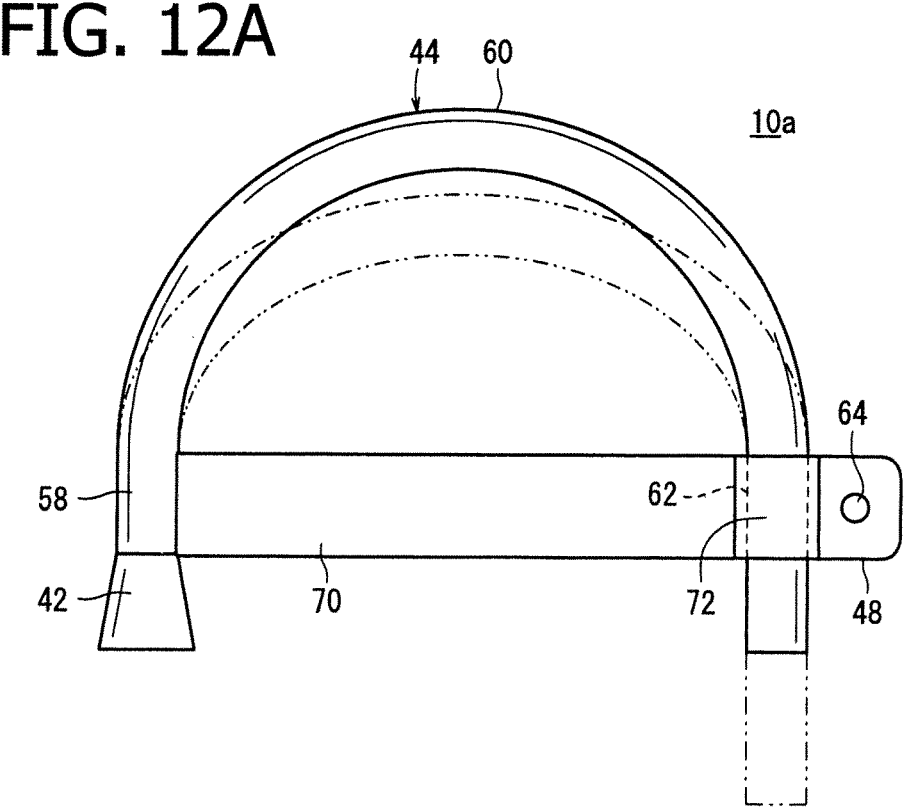
FIG. 12A is a plan view of a direction changing device according to a first modification of the first embodiment.
Figure 12B:
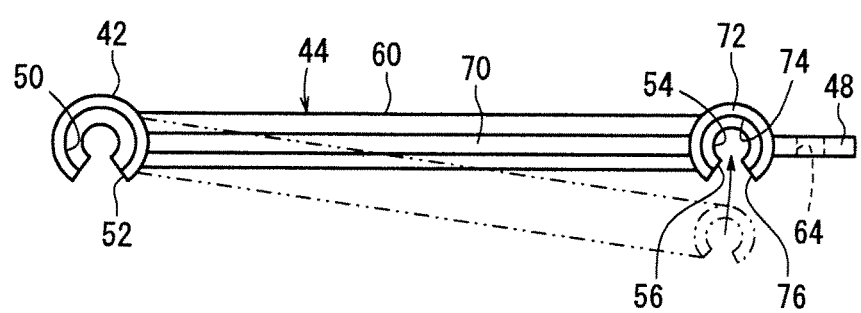
FIG. 12B is a front elevational view of the direction changing device.

As shown in FIGS. 12A and 12B, the direction changing device 10a according to this modification differs from the above-described direction changing device 10 in the configuration of interconnecting section 70. Specifically, the interconnecting section 70 is not provided integrally with the end portion or mounting section 62 of direction changing section 44 and instead is formed with a joint section 72 from which an end portion of the direction changing section 44 is detachable, and the joint section 72 is integrally provided with a locking section 48.

The joint section 72 is configured to have a tubular shape, and has an mounting bore 74 to which the end of the direction changing section 44 can be mounted. The joint section 72 has a slit 76 formed in its outer circumferential surface that communicates with the mounting bore 74, along the entire length of the joint section 72.

According to the direction changing device 10a in this modification, a selected portion of the direction changing section 44 or the mounting section 62 thereof can be mounted into the mounting bore 74 through the slit 76 in the joint section 72. In addition, the selected portion of the direction changing section 44 mounted into the mounting bore 74 can be detached through the mounting bore 74.

This allows for the position of where the portion of the direction changing section 44 is to be mounted to the joint section 72 to be changed. At the time of mounting the direction changing device 10a to the shaft 22 of the catheter 16, therefore, the frictional resistance generated between the shaft 22 and the direction changing device 10a can be adjusted according to the operator's preference. Where the direction changing device 10a is provided on the sheath tube 28, the curvature or radius of curvature of the direction changing section 44 (intermediate section 60) can be changed. Consequently, the frictional resistance generated between the inside surface of the sheath tube 28 and the shaft 22 of the catheter 16 can be adjusted according to the operator's preference.

Second Modification of First Embodiment

A direction changing device 10b according to a second modification of this embodiment will be described below, referring to FIGS. 13A and 13B. In the direction changing device 10b according to this modification, the same components as those of the direction changing device 10a according to the first modification described above are denoted by the same reference symbols as used above, and detailed descriptions of them will be omitted.

Figure 13A:
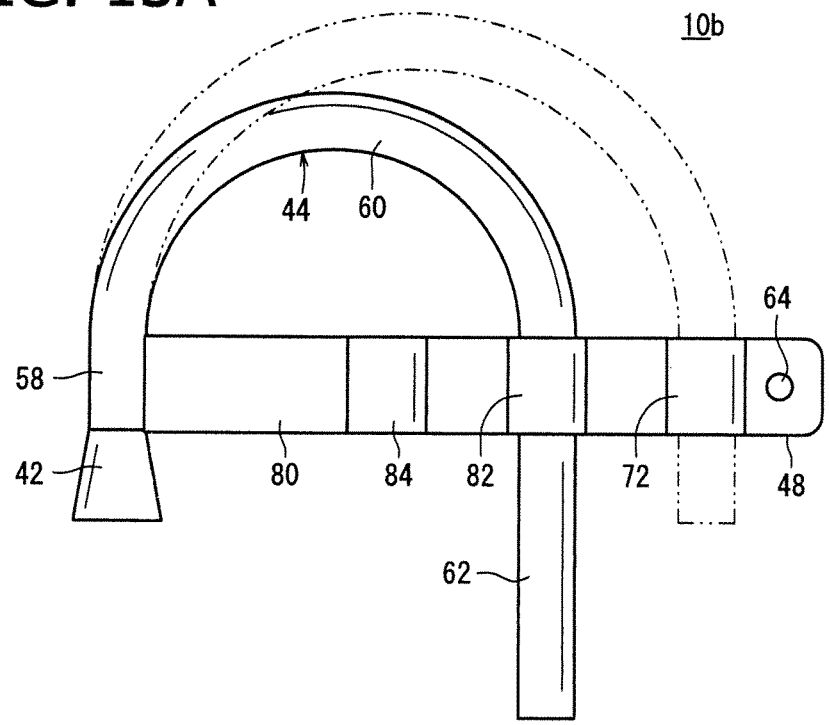
FIG. 13A is a plan view of a direction changing device according to a second modification of the first embodiment.
Figure 13B:
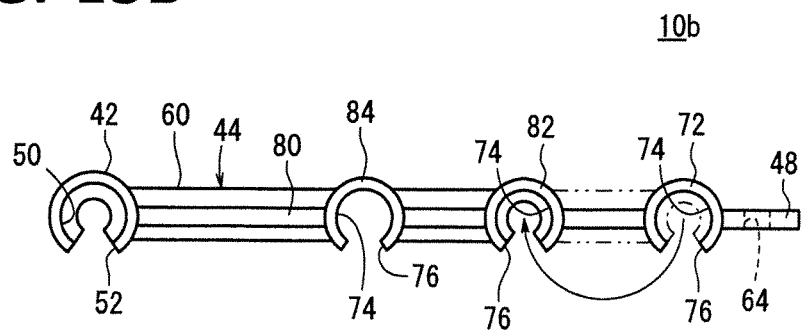
FIG. 13B is a front elevational view of the direction changing device.

As shown in FIGS. 13A and 13B, the direction changing device 10b according to this modification differs from the above-described direction changing device 10a in the configuration of interconnecting section 80. Specifically, the interconnecting section 80 is formed with plural (in this modification, two) joint sections 82, 84 which are the same in configuration as the above-mentioned joint section 72. The joint section 82 is located on the first mounting section 58 side of the joint section 72, and the joint section 84 is located on the first mounting section 58 side of the joint section 82. The intervals between the joint sections 72, 82, 84 can be set arbitrarily.

According to this modification, the curvature or radius curvature of the direction changing section 44 can be changed from when the direction changing section 44 is mounted to the mounting bore 74 of the joint section 72 and when the direction changing section 44 is mounted to the mounting bore 74 of the joint section 82 (or the joint section 84). Therefore, the frictional resistance generated between the shaft 22 of the catheter 16 and the direction changing device 10b or the frictional resistance generated between the inside surface of the sheath tube 28 and the shaft 22 of the catheter 16 can be adjusted according to the operator's preference.

Third Modification of First Embodiment

Figure 14A:
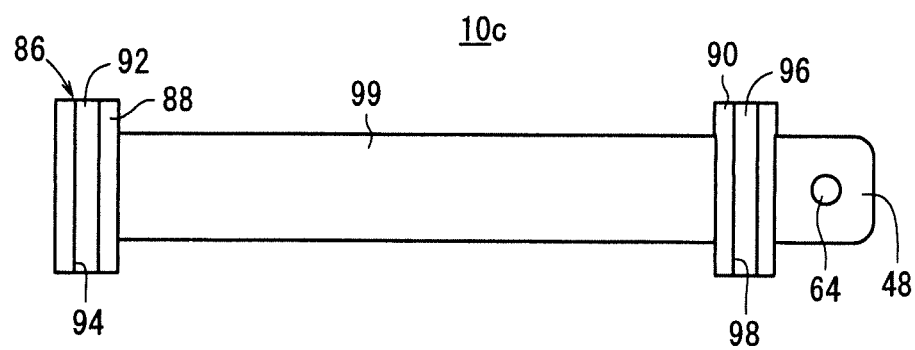
FIG. 14A is a plan view of a direction changing device according to a third modification of the first embodiment.
Figure 14B:
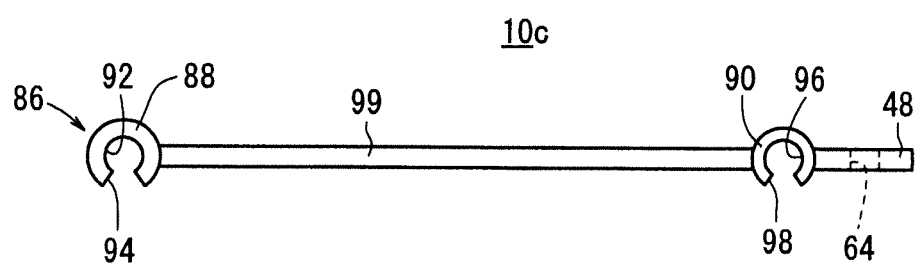
FIG. 14B is a front elevational view of the direction changing device.

A direction changing device 10c according to a third modification of this embodiment will be described below, referring to FIGS. 14A to 15B. As shown in FIGS. 14A and 14B, the direction changing device 10c according to this modification differs from the above-described direction changing device 10 in the configuration of direction changing section 86. In this modification, the above-mentioned tapered section 42 is omitted.

The direction changing section 86 has a first mounting section 88 and a second mounting section 90 to which the sheath tube 28 can be mounted. In other words, the direction changing section 86 is not provided with the intermediate section 60, which has been present in the above-mentioned direction changing section 44. The first mounting section 88 has a bore 92 with a predetermined inside diameter sized for receiving the sheath tube 28 therein. In addition, the first mounting section 88 is formed with a slit 94 in its outer circumferential surface that communicates with the bore 92, and having a constant width over the entire length of the first mounting section 88.

The second mounting section 90 has the same configuration as the first mounting section 88. Specifically, the second mounting section 90 is formed with a bore 96 in which the sheath tube 28 can be disposed, and with a slit 98 communicating with the bore 96 and opening to the outer circumferential surface of the second mounting section 90.

In addition, an interconnecting section 99 in this modification is the same in configuration as the above-mentioned interconnecting section 46. Thus, the interconnecting section 99 alone constitutes a holding section which interconnects the first mounting section 88 and the second mounting section 90 and which maintains the positions of the first and second mounting sections 88, 90 fixed relative to each other. The bore 92 and the bore 96 function similarly to the above-mentioned second receiving bore 54, while the slit 94 and the slit 98 function similarly to the above-mentioned second slit 56.

Figure 15A:
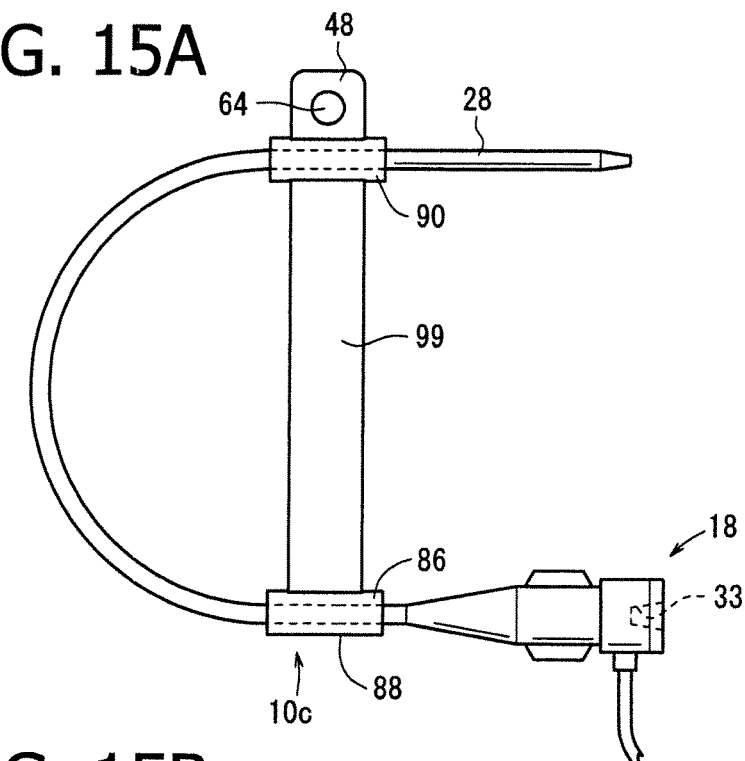
FIG. 15A is an illustration of the direction changing device shown in FIG. 14A mounted to a sheath tube.

According to this modification, in the condition where the sheath tube 28 is mounted to the first mounting section 88 and the second mounting section 90, the sheath tube 28 is held in a curved shape such that the sheath tube portion mounted to the first mounting section 88 extends proximally to distally in one direction and the sheath tube portion mounted to the second mounting section 90 extends proximally to distally in another direction with these directions being opposite to each other (see FIG. 15A).

This ensures that at the time of inserting the catheter 16 into the sheath introducer 18, the catheter 16 can be easily manipulated by the operator's dominant hand and, as a result, the catheter 16 can be efficiently inserted into the right leg 107 (into the living body), like in the case of the above-described direction changing device 10.

Figure 15B:
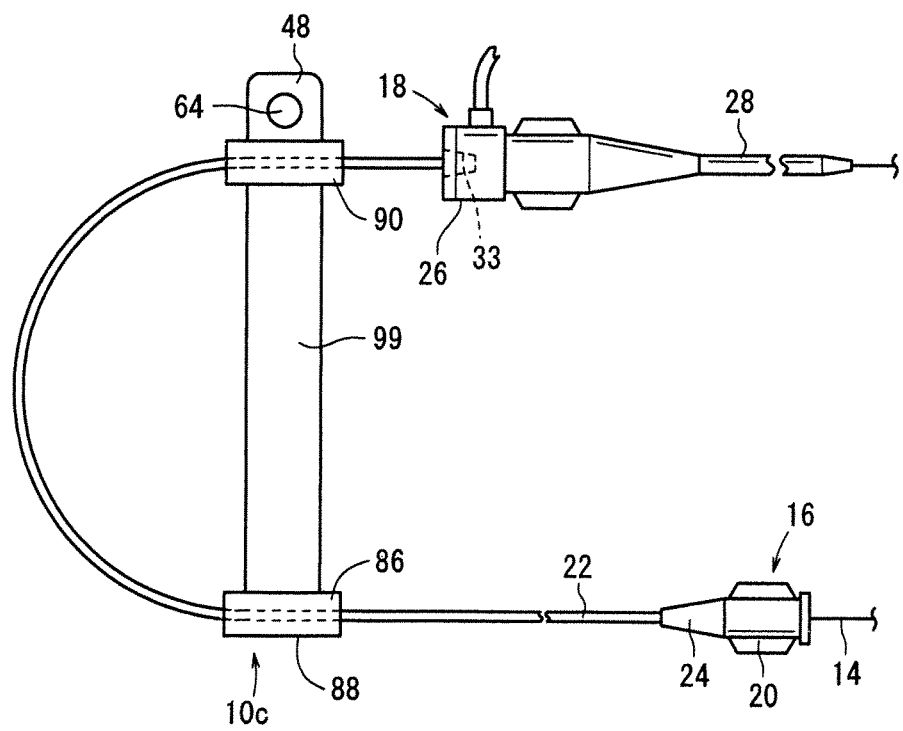
FIG. 15B is an illustration of the direction changing device mounted to a shaft of a catheter.

The direction changing device 10c according to this modification may be mounted to the shaft 22 of the catheter 16 in such a manner that the shaft 22 is movable, as shown in FIG. 15B. In this case, also, the same result as above can be produced.

This modification is not restricted to the above-mentioned configuration. For example, the direction changing device 10c may have a configuration in which the interconnecting section 99 is omitted, and a lateral portion of the first mounting section 88 and a lateral portion of the second mounting section 90 are directly joined to each other.

Second Embodiment

Now, a medical assembly 12A according to a second embodiment of the present invention will be described below, referring to FIGS. 16 to 26C. In the medical assembly 12A according to this embodiment, the same components as those of the above-described medical apparatus assembly 12 are denoted by the same reference symbols as used above, and detailed descriptions of them will be omitted.

As shown in FIG. 16, a sheath hub 26 of a sheath introducer 18 of the medical assembly 12A is a hollow member formed from a resin or the like. The sheath hub 26 includes a hub rear end section 25 having a hollow cylindrical shape, a hub intermediate section 27 which is a hollow cylindrical body smaller than the hub rear end section 25 in its outside diameter, a pair of projection pieces 29 projecting from an outer circumferential surface of the hub intermediate section 27, and a hub distal end section 31 which is provided at the distal end of the hub intermediate section 27 and tapers down in a distal direction. The sheath hub 26 may also have a configuration in which the pair of projection pieces 29 and the hub distal end section 31 are omitted.

At a rear end face (proximal end face) of the hub rear end section 25, an opening of a catheter insertion port 33 into which a shaft 22 of a catheter 16 can be inserted is provided.

In the bore on the proximal side in the hub rear end section 25 is disposed the above-mentioned valve element (check valve) (not shown) for preventing a liquid such as blood from leaking out. Incidentally, a branch tube 30 is connected through a branch connector 35 to a lateral side of a proximal portion of the sheath hub 26, at an axial position that is distal of the valve element.

Figure 17:
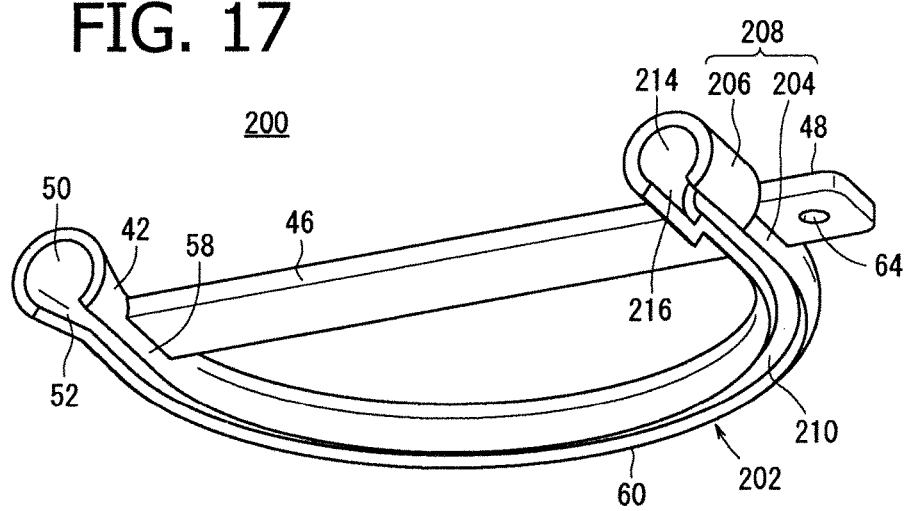
FIG. 17 is a perspective view of the direction changing device shown in FIG. 16.
Figure 18:
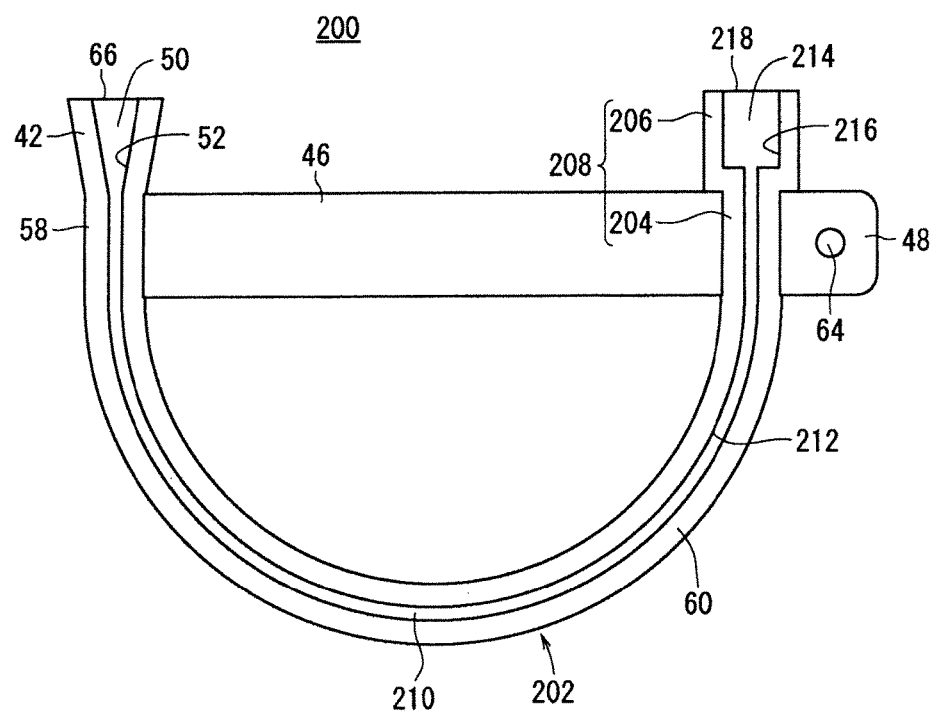
FIG. 18 is a plan view of the direction changing device shown in FIG. 16.
Figure 19:
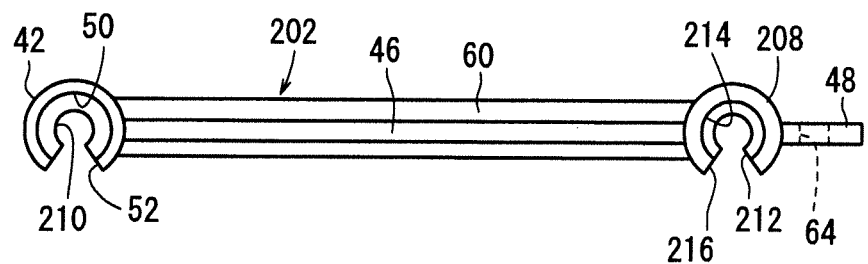
FIG. 19 is a front elevational view of the direction changing device shown in FIG. 16.

As shown in FIGS. 17 to 19, a direction changing device 200 of the medical assembly 12A includes a tapered section 42, a direction changing section 202 formed to be continuous with the tapered section 42 and roughly U-shaped in plan view, a plate-shaped interconnecting section 46 provided on the direction changing section 202, and a plate-shaped locking section 48 for locking or securing the direction changing section 202 to the patient 106 or the like.

The direction changing section 202 includes a first mounting section 58 continuous with the tapered section 42, an intermediate section 60 continuous with the first mounting section 58, and a second mounting section 208 which is continuous with the intermediate section 60 and which has a small diameter portion 204 and a large diameter portion 206.

The first mounting section 58, the intermediate section 60, and the small diameter portion 204 are integrally formed as a tube or tubular body having a constant outside diameter, which has a lumen (second receiving bore 210) with a constant inside diameter through which the shaft 22 of the catheter 16 can be inserted and passed.

The second receiving bore 210 communicates with a first receiving bore 50. In addition, the tube body has a second slit 212 formed in its outer circumferential surface which communicates with the second receiving bore 210, and has a constant width along the entire length thereof (see FIG. 18).

The second slit 212 gradually narrows in width in the radial direction toward the second receiving bore 210 (see FIG. 19). In other words, the second slit 212 is formed so that its width gradually decreases along the radial direction from the outer circumferential surface toward the inner circumferential surface (the wall surface defining the second receiving bore 210) of the direction changing section 202. The second slit 212 communicates with the first slit 52.

The large diameter portion 206 of the second mounting section 208 is continuous with the small diameter portion 204, and has a third receiving bore 214 formed therein in which the hub rear end section 25 of the sheath introducer 18 can be disposed (mounted). The third receiving bore 214, formed to be larger than the second receiving bore 210 in diameter, communicates with the second receiving bore 210. Thus, the first receiving bore 50, the second receiving bore 210 and the third receiving bore 214 together constitute a single receiving bore.

The large diameter section 206 has a third slit 216 formed in its outer circumferential surface with a constant width and which communicates with the third receiving bore 214, over substantially the entire length of the large diameter section 206 (see FIG. 18). The third slit 216 gradually narrows in width as it extends radially toward the third receiving bore 214 (see FIG. 19).

In other words, the third slit 216 is formed so that its width gradually decreases along the direction from the outer circumferential surface of the large diameter section 206 toward the wall surface defining the third receiving bore 214. The third slit 216 communicates with the second slit 212. Thus, the first slit 52, the second slit 212 and the third slit 216 together constitute a single slit.

The interconnecting section 46 joins one end portion and the other end portion of the direction changing section 202. In other words, the interconnecting section 46 interconnects the first mounting section 58 and the second mounting section 208. This ensures that the shape of the direction changing section 202 can be held in a roughly U-shaped form in plan view.

The locking section 48, provided on the other end side of the direction changing section 202, is opposed to the interconnecting section 46. The locking section 48 has a hole 64 formed centrally therein through which a suture 112 (see FIG. 21) is to be passed.

In the direction changing device 200 configured as above, the axial direction of the first mounting section 58 (the direction in which the second receiving bore 210 extends in the first mounting section 58) and the axial direction of the second mounting section 208 (the direction in which the third receiving bore 214 extends in the second mounting section 208) are parallel to each other in plan view.

When the shaft 22 of the catheter 16 is slidably mounted in the first mounting section 58 and the sheath hub 26 of the sheath introducer 18 is mounted in the second mounting section 208, the shaft portion in the first mounting section 58 extends proximally to distally in one direction (first direction; the leftward direction in FIG. 16), and the sheath introducer portion mounted in the second mounting section 208 extends proximally to distally in another direction (second direction; the rightward direction in FIG. 16) with these directions being opposite to each other.

In addition, the intermediate section 60 and the interconnecting section 46 function as a holding section which interconnects the first mounting section 58 and the second mounting section 208 and which fixes the positions of the first mounting section 58 and the second mounting section 208 relative to each other. This makes it possible to suitably restrain any relative change of the first direction and the second direction.

Furthermore, an aperture (first aperture 66) opening to one end face of the tapered section 42 and an aperture (second aperture 218) opening to the other end face of the direction changing section 202 (the other end face of the second mounting section 208) are oriented to open and face in substantially the same direction, instead of being oriented opposite to each other (see FIG. 18).

Figure 20:
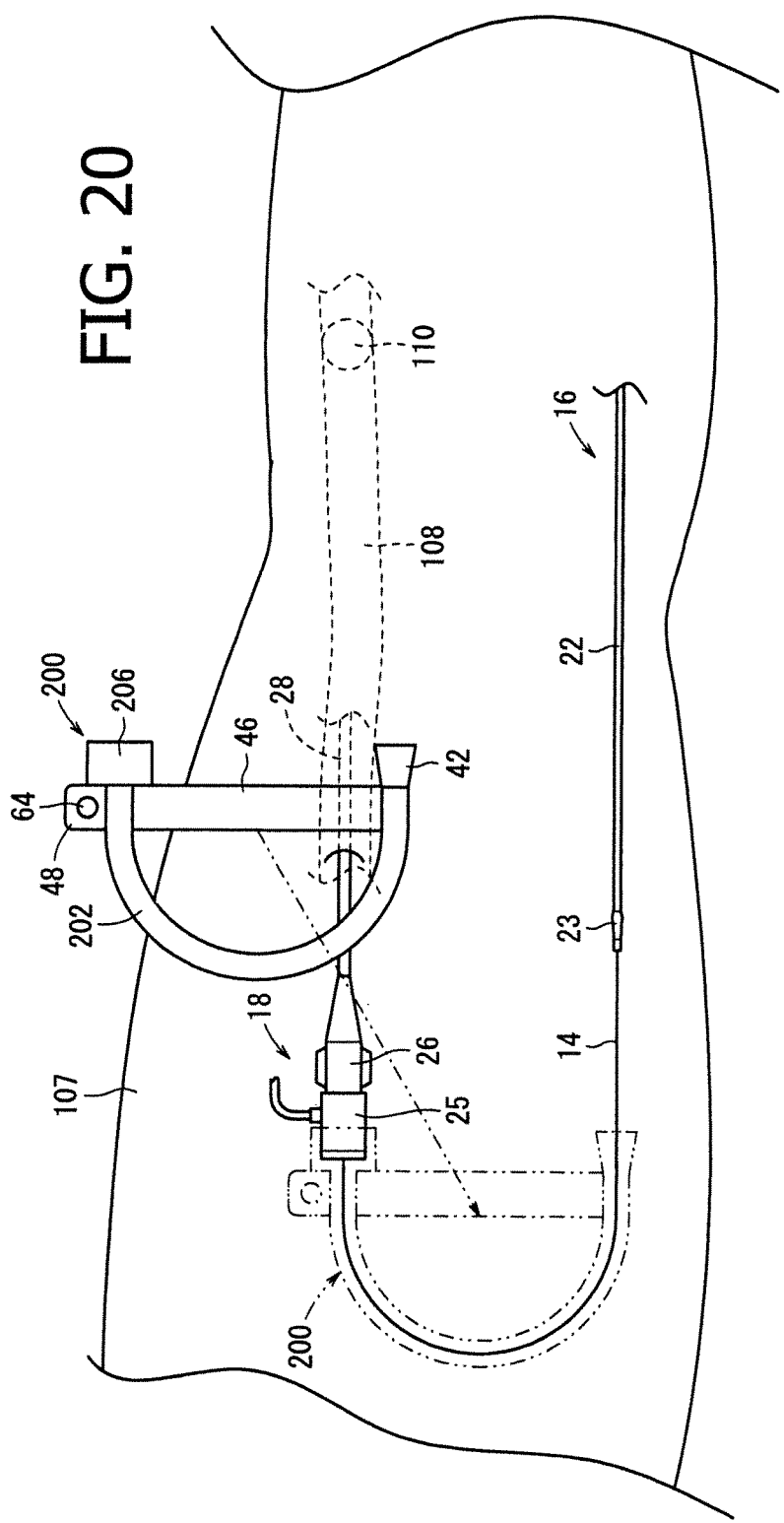
FIG. 20 is an illustration of the mounting of the direction changing device shown in FIG. 16 to a sheath introducer.

In this embodiment, after placing the sheath tube 28 in the right leg 107, the operator 102 mounts the direction changing device 200 to the sheath introducer 18 (see FIG. 20).

Specifically, a portion of the hub rear end section 25 of the sheath introducer 18 is mounted in the third receiving bore 214 via the third slit 216 of the direction changing device 200. In addition, a guidewire 14 is inserted into the first receiving bore 50 and the second receiving bore 210 via the first slit 52 and the second slit 212 of the direction changing device 200, while curving the guidewire 14 into a roughly U-shaped form.

Here, in this embodiment, the direction changing device 200 is flexible. The width of the third slit 216 gradually narrows along the direction from the outer circumferential surface of the large diameter part 206 toward the wall surface defining the third receiving bore 214. Therefore, for example by locating the hub rear end section 25 at the third slit 216 and pressing the hub rear end section 25 toward the third receiving bore 214, the wall portions defining the third slit 216 can be elastically deformed outward and the slit width can be thereby expanded.

This ensures that the hub rear end section 25 can be easily mounted into the third receiving bore 214. After a portion of the hub rear end section 25 is mounted into the third receiving bore 214, the wall portions defining the third slit 216 return to their original shape, so that the hub rear end section 25 will not slip out of the bore 214 via the third slit 216 thus providing the hub section 25 with a snap-fit connection in the bore 214.

Similarly, the width of the first slit 52 gradually narrows along the direction from the outer circumferential surface toward the inner circumferential surface of the tapered section 42, and the width of the second slit 212 gradually narrows along the direction from the outer circumferential surface toward the inner circumferential surface of the direction changing section 202. Therefore, the guidewire 14 can be easily mounted into the first receiving bore 50 and the second receiving bore 210. Moreover, the guidewire 14 can be suitably restrained from slipping out of these bores 50 and 210.

Figure 21:
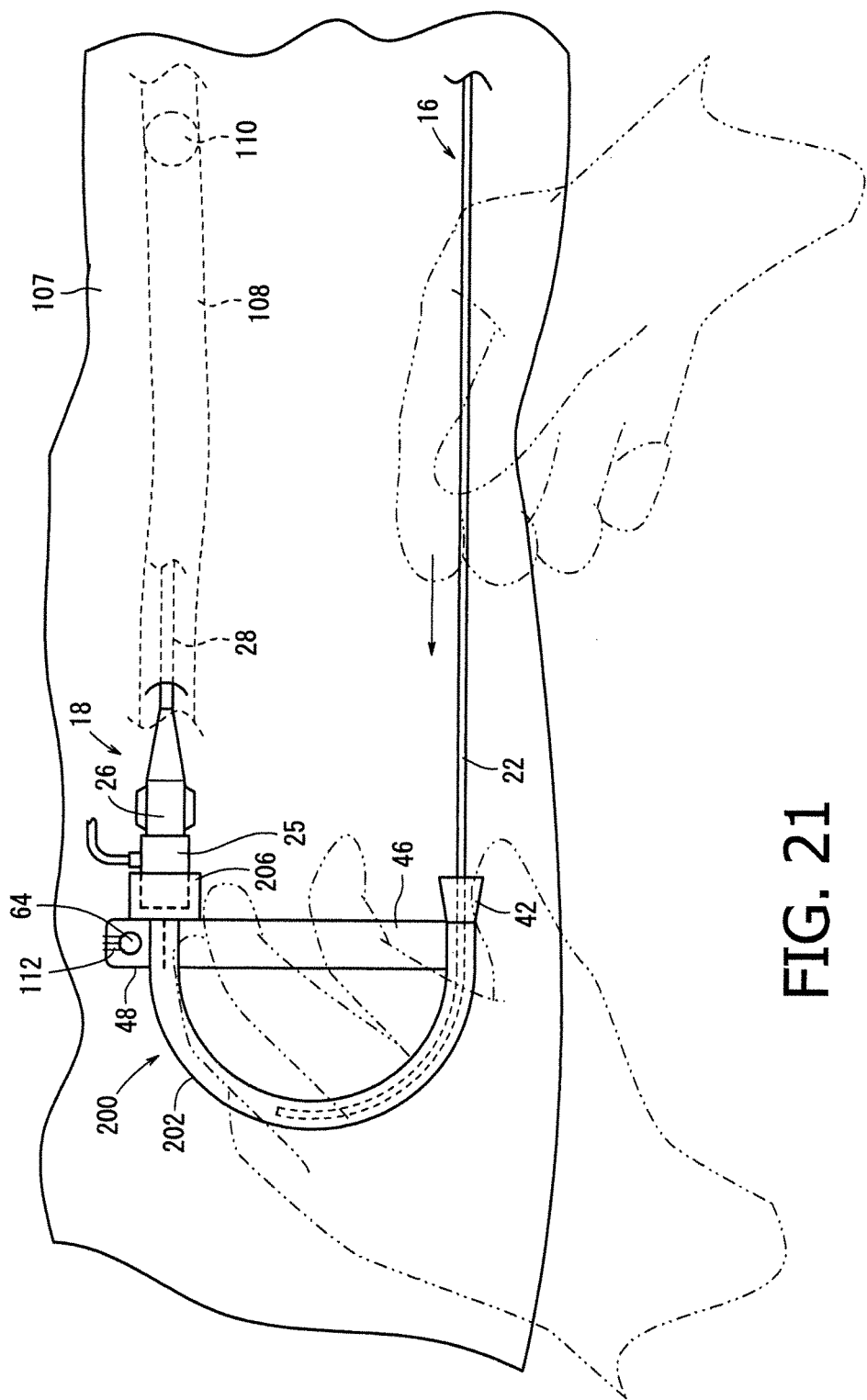
FIG. 21 is an illustration of a shaft of a catheter being inserted into a receiving bore of the direction changing device shown in FIG. 16.
Figure 22:
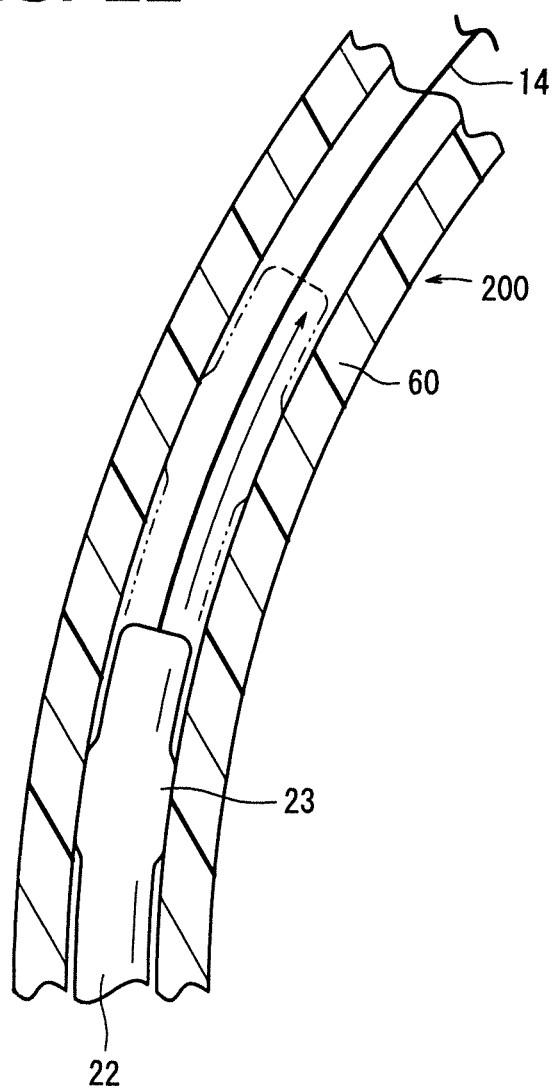
FIG. 22 is a fragmenting sectional illustration of the shaft of the catheter being passed through the receiving bore of the direction changing device shown in FIG. 16.

Subsequently, the operator 102 sutures the locking section 48 of the direction changing device 200 and the skin of the patient 106 to each other with a suture 112 (see FIG. 21). This causes the direction changing device 200 to be secured or locked to the patient 106. Like with the first embodiment, the locking section 48 may be sutured to a cover body (drape or the like) covering the patient 106, instead of the skin of the patient 106.

In this condition, the catheter insertion port 33 of the sheath hub 26 is oriented to open toward and face the left side, whereas the first aperture 66 of the direction changing device 200 (the aperture at one end of the first receiving bore 50) is oriented to open toward and face the right side.

Consequently, the direction of insertion of the sheath tube 28 into the right leg 107 and the direction of insertion of the shaft 22 of the catheter 16 into the first receiving bore 50 of the direction changing device 200 are opposite to each other. Specifically, the direction of insertion of the sheath tube 28 into the right leg 107 is rightward, whereas the direction of insertion of the shaft 22 into the first receiving bore 50 is leftward.

Therefore, the operator 102 can easily insert the shaft 22 of the catheter 16 into the catheter insertion port 33 of the sheath hub 26 by inserting the shaft 22 into the first receiving bore 50 of the direction changing device 200 and advancing the shaft 22 through the second receiving bore 210 (see FIG. 22), while manipulating the catheter 16 with their right hand, which for a right-handed operator is the dominant hand.

Figure 23:
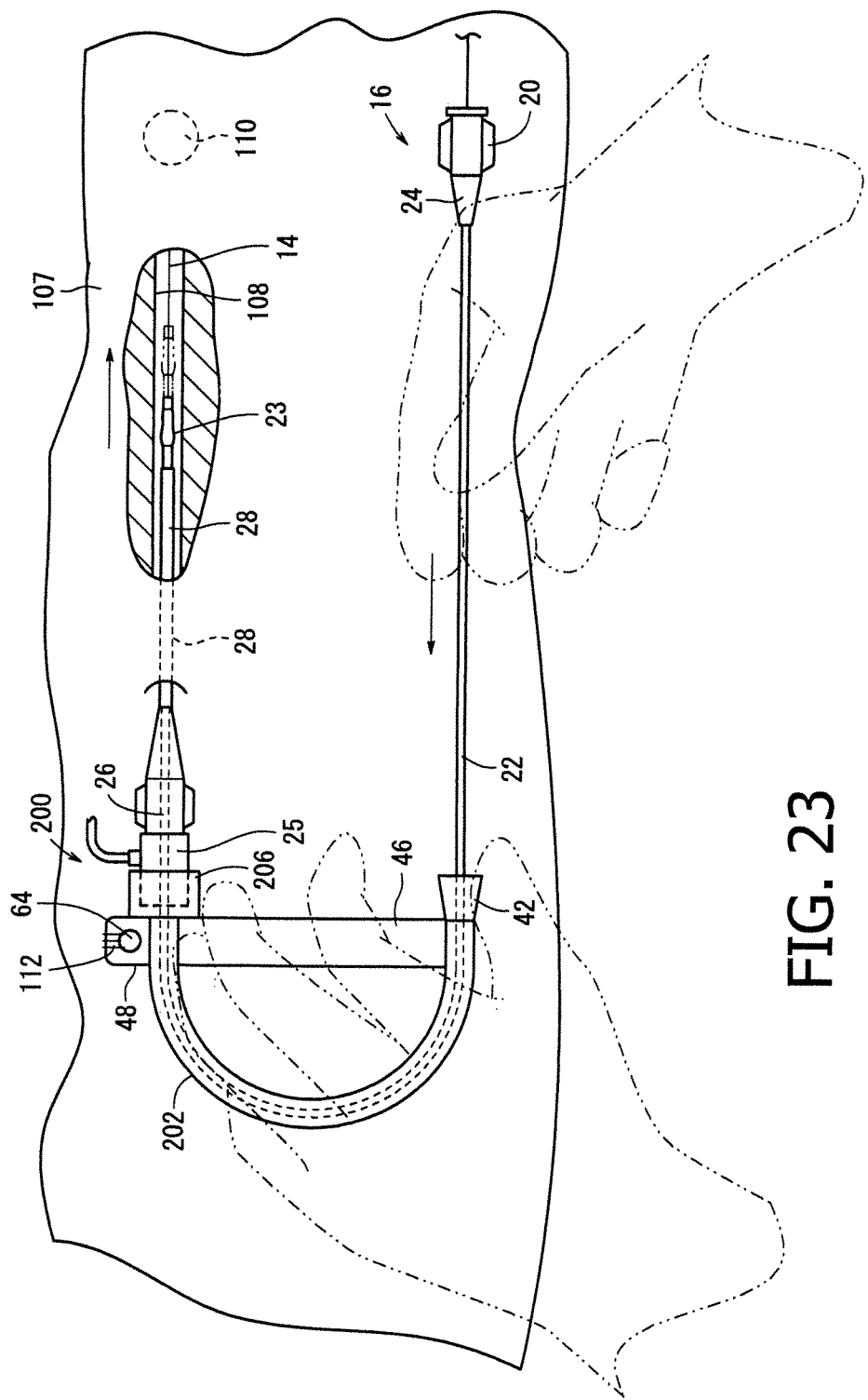
FIG. 23 is an illustration of the shaft of the catheter being inserted into the sheath introducer to thereby advance the shaft within a blood vessel.

Then, the shaft 22 of the catheter 16 inserted into the lumen of the sheath hub 26 is passed through the lumen of the sheath tube 28, to be inserted into the superficial femoral artery 108 (FIG. 23).

Thereafter, the operator 102 delivers the balloon part 23 of the shaft 22 of the catheter 16 to the lesion 110, and inflates the balloon part 23 in situ, thereby treating the lesion 110.

According to this embodiment, in the condition where the axial direction of the first mounting section 58 and the axial direction of the second mounting section 208 are parallel to each other in plan view, and where the hub rear end section 25 of the sheath introducer 18 is mounted in the second mounting section 208 and the shaft 22 of the catheter 16 is slidably mounted in the first mounting section 58, the shaft 22 will adopt a curved shape such that the catheter portion mounted in the first mounting section 58 extends proximally to distally in one direction and the sheath introducer portion mounted in the second mounting section 208 extends proximally to distally in another direction with these directions being opposite to each other. Therefore, the direction of insertion of the sheath introducer 18 into the living body and the insertion direction for the catheter 16 into the device 200 are opposite to each other.

This ensures that at the time of inserting the catheter 16 into the sheath introducer 18, the catheter 16 can be easily manipulated by the operator's dominant hand. Consequently, the catheter 16 can be efficiently inserted into the living body.

In addition, since the hub rear end section 25 formed with the catheter insertion port 33 is mounted to the large diameter part 206, the catheter insertion port 33 is restrained from shifting by the large diameter part 206. In other words, positional deviation between the second receiving bore 210 formed in the small diameter part 204 and the catheter insertion port 33 can be favorably restricted. This enables easy insertion of the catheter 16 into the sheath introducer 18.

Furthermore, according to this embodiment, the shaft 22 of the catheter 16 can be guided by the intermediate section 60 from the first mounting section 58 to the small diameter part 204 of the second mounting section 208. Therefore, the shaft 22 can be inserted into the sheath introducer 18 more easily.

In this embodiment, the direction changing section 202 is formed in a roughly U-shaped form in plan view. Therefore, the shaft 22 of the catheter 16 mounted in the second receiving bore 210 of the direction changing section 202 is also curved into a roughly U-shaped form in plan view. This permits the shaft 22 of the catheter 16 to be advanced within the second receiving bore 210 comparatively smoothly. Consequently, the shaft 22 can be smoothly inserted into the sheath introducer 18.

The direction changing device 200 according to this embodiment is formed with the first slit 52 communicating with the first receiving bore 50, and formed with the second slit 212 communicating with the second disposing hole 210. Therefore, the guidewire 14 (the shaft 22) can be easily mounted into the first receiving bore 50 and the second receiving bore 210 via the first slit 52 and the second slit 212.

Furthermore, the direction changing device 200 is formed with the third slit 216 communicating with the third receiving bore 214. Therefore, a part of the hub rear end section 25 can be easily mounted into the third receiving bore 214 through the third slit 216.

This ensures that mounting of the direction changing device 200 to the sheath introducer 18 can be performed after the insertion of a distal portion of the sheath tube 28 into the right leg 107 of the patient 106. Accordingly, at the time of inserting the distal portion of the sheath tube 28 into the right leg 107, it is possible to obviate the situation in which the inserting operation might be obstructed by the direction changing device 200.

In this embodiment, the locking section 48 and the skin of the patient 106 are sutured to each other with the suture 112, thereby locking the locking section 48 to the patient 106. Therefore, at the time of inserting the shaft 22 of the catheter 16 into the sheath introducer 18, the sheath tube 28 can be suitably inhibited from slipping out of the right leg 107. Incidentally, in the medical apparatus assembly 12A according to this embodiment, naturally, the direction changing device 200 also may be mounted to the sheath introducer 18 before its tube 28 is inserted into the patient's leg 107, as shown in FIG. 16.

This embodiment is not restricted to the above-mentioned configuration. For instance, in the direction changing device 200 according to this embodiment, the interconnecting section 46 may be omitted. In that case, the intermediate section 60 alone constitutes the holding section by which the first mounting section 58 and the second mounting section 208 are interconnected and their positions are fixed relative to each other. In such a configuration, also, the direction changing section 202 can be held in a roughly U-shaped form in plan view.

First Modification of Second Embodiment

A direction changing device 200a according to a first modification of this embodiment will be described below, referring to FIGS. 24A and 24B. In the direction changing device 200a according to this modification, the same components as those of the above-described direction changing device 200 are denoted by the same reference symbols as used above, and detailed descriptions of them will be omitted. The same applies also to a direction changing device 200c according to a third modification which will be described later.

Figure 24A:
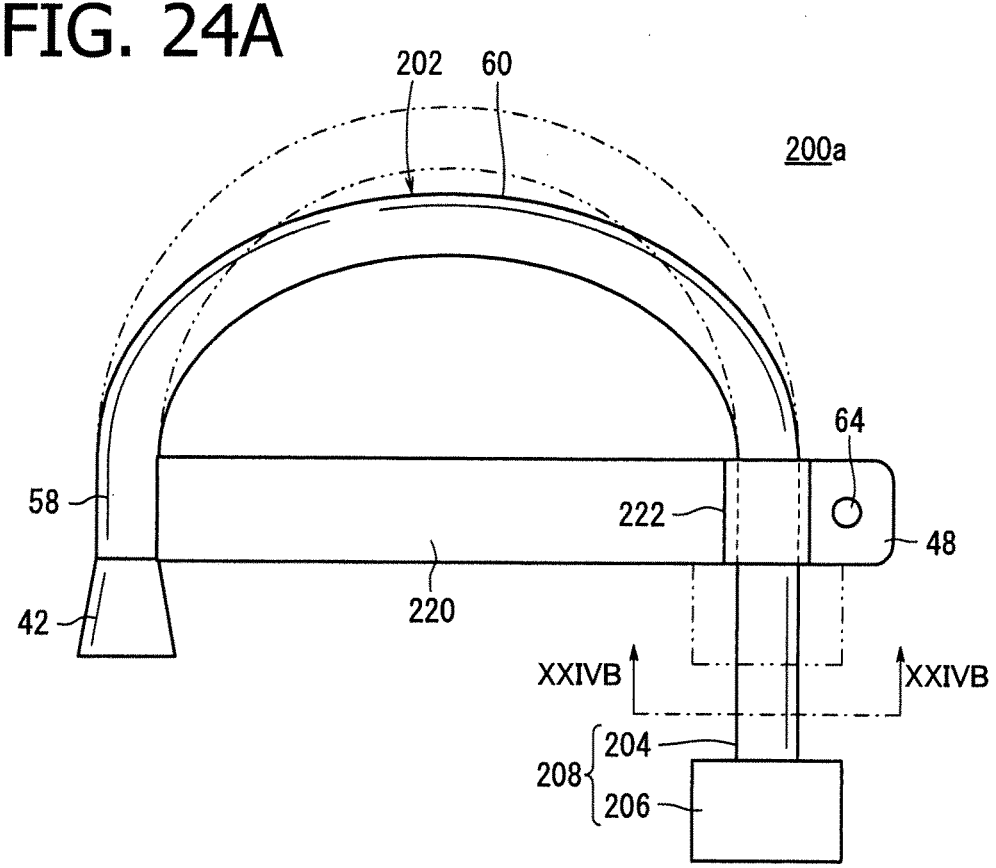
FIG. 24A is a plan view of a direction changing device according to a first modification of the second embodiment.
Figure 24B:
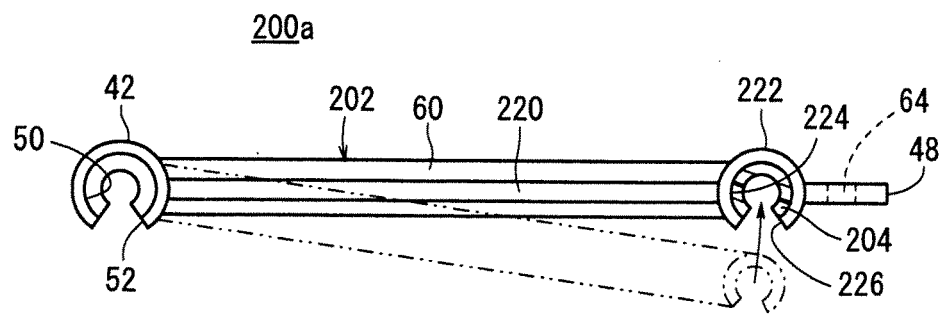
FIG. 24B is a sectional front view taken along line XXIVB-XXIVB of FIG. 24A.

As shown in FIGS. 24A and 24B, the direction changing device 200a according to this modification differs from the above-described direction changing device 200 in the configuration of an interconnecting section 220. Specifically, the interconnecting section 220 has a configuration in which one end portion of a direction changing section 202 is not integrally formed therewith; instead, there is formed a joint section 222 to which the one end portion of the direction changing section 202 can be detachably mounted. A locking section 48 is provided integrally with the joint section 222.

The joint section 222 is formed to have a tubular shape, and has a mounting bore 224 to which the end portion of the direction changing section 202 can be mounted. In addition, the joint section 222 has a slit 220 formed in its outer circumferential surface which communicating with the mounting bore 224, along the entire length of the joint section 222.

According to the direction changing device 200a of this modification, a selected portion of the one end portion of the direction changing section 202 can be mounted into the mounting bore 224 via the slit 226 of the joint section 222. The selected portion of the direction changing section 202 that is mounted in the mounting hole 224 likewise can be detached through the slit 226.

This allows for the position at which the end portion of the direction changing section 202 is mounted to the joint section 222 to be changed. Therefore, the frictional resistance generated between the shaft 22 and the direction changing device 200a can be suitably adjusted according to the operator's preference.

Second Modification of Second Embodiment

A direction changing device 200b according to a second modification of this embodiment will be described below, referring to FIGS. 25A and 25B. In the direction changing device 200b according to this modification, the same components as those of the direction changing device 200a of the first modification described above are denoted by the same reference symbols as used above, and detailed descriptions of them will be omitted.

Figure 25A:
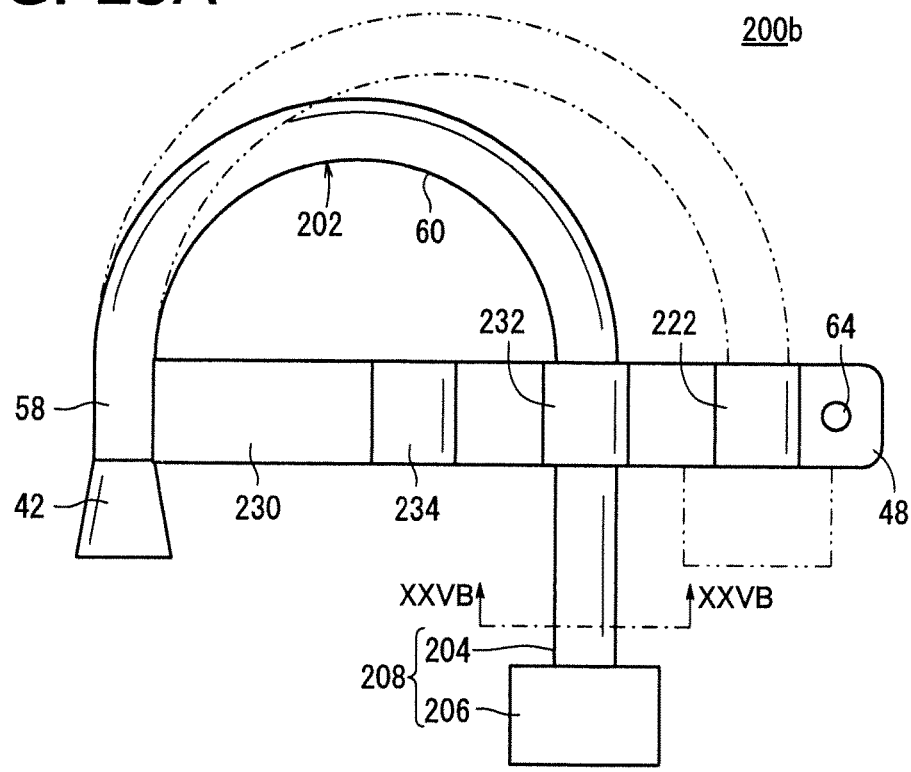
FIG. 25A is a plan view of a direction changing device according to a second modification of the second embodiment.
Figure 25B:
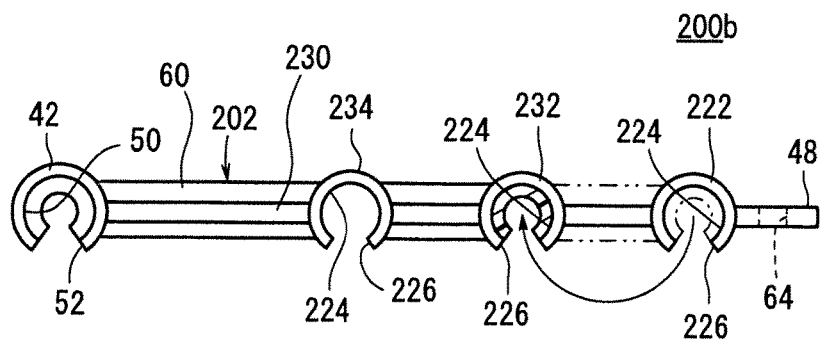
FIG. 25B is a sectional front view taken along line XXVB-XXVB of FIG. 25A.

As shown in FIGS. 25A and 25B, the direction changing device 200b according to this modification differs from the above-described direction changing device 200a in the configuration of interconnecting section 230. Specifically, the interconnecting section 230 is formed further with plural (in this modification, two) joint sections 232 and 234 which are the same as the above-mentioned joint section 222 in configuration. The joint section 232 is located on the first mounting section 58 side of the joint section 222, and the joint section 234 is located on the first mounting section 58 side of the joint section 232. The intervals of the joint sections 222, 232 and 234 can be set arbitrarily.

According to this modification, it is possible to change the curvature or radius of curvature of the direction changing section 202, from when the direction changing section 202 is mounted into the mounting bore 224 of the joint section 222 and when the direction changing section 202 is mounted into the mounting bore 224 of the joint section 232 (or the joint section 234). Therefore, the frictional resistance generated between the shaft 22 of the catheter 16 and the direction changing device 200b can be suitably adjusted according to the operator's preference.

Third Modification of Second Embodiment

Figure 26A:
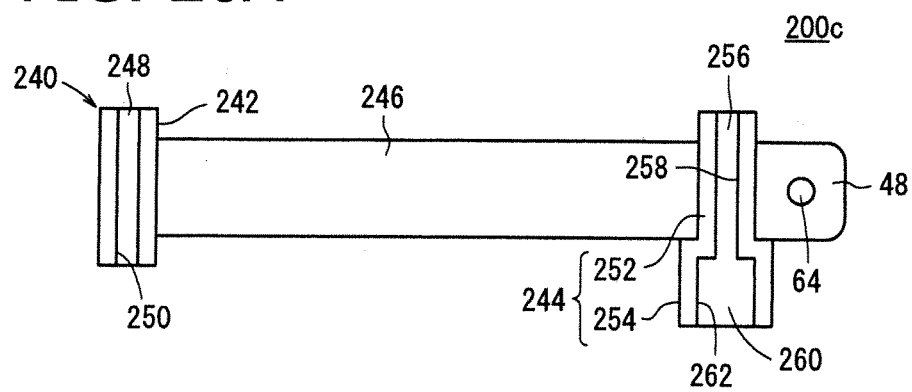
FIG. 26A is a plan view of a direction changing device according to a third modification of the second embodiment.
Figure 26B:
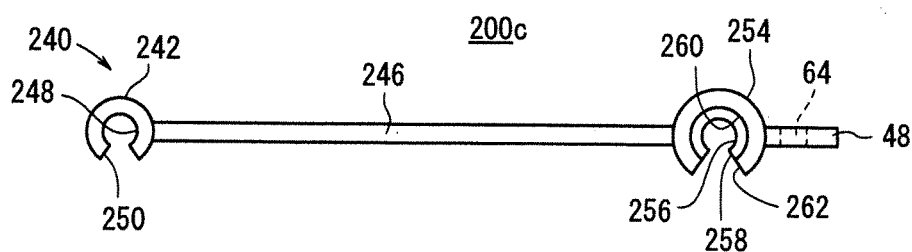
FIG. 26B is a front elevational view of the direction changing device.
Figure 26C:
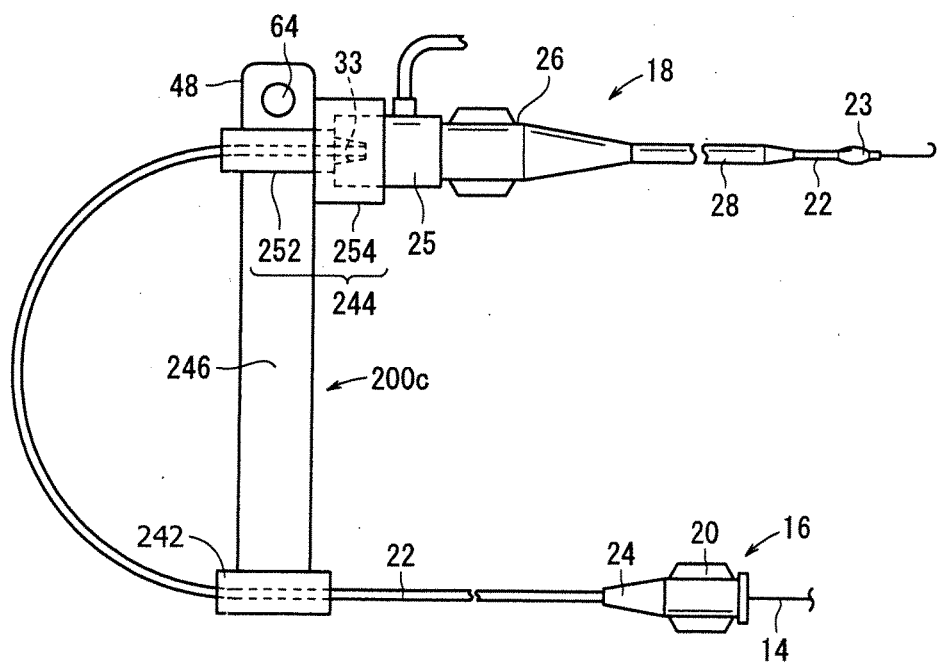
FIG. 26C is an illustration of a shaft of a catheter being inserted in a sheath introducer to which the direction changing device is mounted.

A direction changing device 200c according to a third modification of this embodiment will be described below, referring to FIGS. 26A to 26C. As shown in FIGS. 26A to 26C, the direction changing device 200c according to this modification differs from the above-described direction changing device 200 in the configuration of direction changing section 240. In this modification, the above-mentioned tapered section 42 is omitted.

The direction changing section 240 includes a first mounting section 242, a second mounting section 244, and an interconnecting section 246 which interconnects the first mounting section 242 and the second mounting section 244. Specifically, the direction changing section 240 is not provided with the intermediate section 60 present in the above-mentioned direction changing section 202. The first mounting section 242 has a bore 248 with a predetermined inside diameter sized for receiving the shaft 22 of the catheter 16 therein. In addition, the first mounting section 242 is formed with a slit 250 in its outer circumferential surface communicating with the bore 248, over the entire length of the first mounting section 242.

The second mounting section 244 has a small diameter portion 252 and a large diameter portion 254. The small diameter portion 252 is provided therein with a bore 256 in which the shaft 22 of the catheter 16 can be disposed. The small diameter portion 252 has a slit 258 formed in its outer circumferential surface communicating with the bore 256, and having a constant width over the entire length of the small diameter part 252.

The large diameter section 254 is provided therein with bore 260 which communicates with the bore 256 and in which a portion of the hub rear end section 25 of the sheath introducer 18 can be disposed. The large diameter portion 254 has a slit 262 formed in its outer circumferential surface communicating with the bore 260, over substantially the entire length of the large diameter portion 254. The slit 258 and the slit 262 communicate with each other.

In addition, the interconnecting section 246 in this modification is the same as the above-mentioned interconnecting section 46 in configuration. The interconnecting section 246 alone constitutes a holding section by which the first mounting section 242 and the second mounting section 244 are interconnected so that their positions are fixed relative to each other.

According to this modification, when the hub rear end section 25 is mounted to the large diameter portion 254 of the second mounting section 244 and the shaft 22 of the catheter 16 is disposed in the bore 248 in the first mounting section 242 and the bore 256 in the small diameter portion 252, the shaft 22 adopts a roughly U-shaped curved form in plan view. Therefore, the direction of insertion of the sheath introducer 18 into the living body and the insertion direction for the catheter 16 into the device 200c can be set to be substantially opposite to each other.

This ensures that at the time of inserting the catheter 16 into the sheath introducer 18, the catheter 16 can be easily operated by the operator's dominant hand and, as a result, the catheter 16 can be efficiently inserted into the right leg 107 (into the living body), as with the above-described direction changing device 200.

This modification is not restricted to the above-mentioned configuration. For instance, the direction changing device 200c may have a configuration wherein the interconnecting section 246 is omitted and wherein a lateral portion of the first mounting section 242 and a lateral portion of the second mounting section 244 are joined directly to each other.

Third Embodiment

Now, a medical assembly 12B according to a third embodiment of the present invention will be described below, referring to FIGS. 27 and 28. In the medical assembly 12B according to this embodiment, the same components as those of the above-described medical assembly 12A are denoted by the same reference symbols as used above, and detailed description of them will be omitted. The same applies also in a medical assembly 12C according to a fourth embodiment and a medical assembly 12D according to a fifth embodiment which will be described later.

Figure 27:
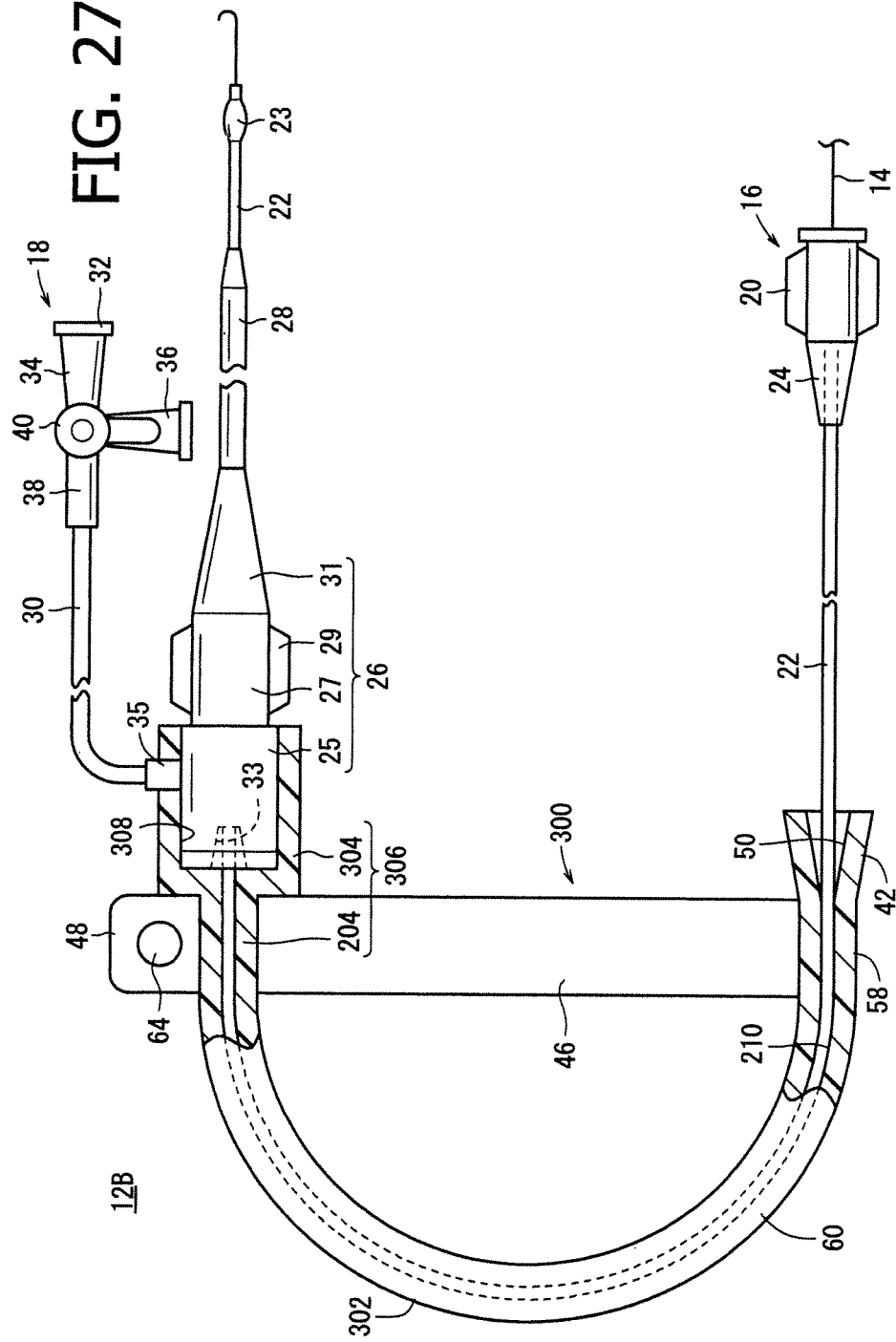
FIG. 27 is a schematic plan view of a medical assembly having a direction changing device according to a third embodiment of the present invention.
Figure 28:
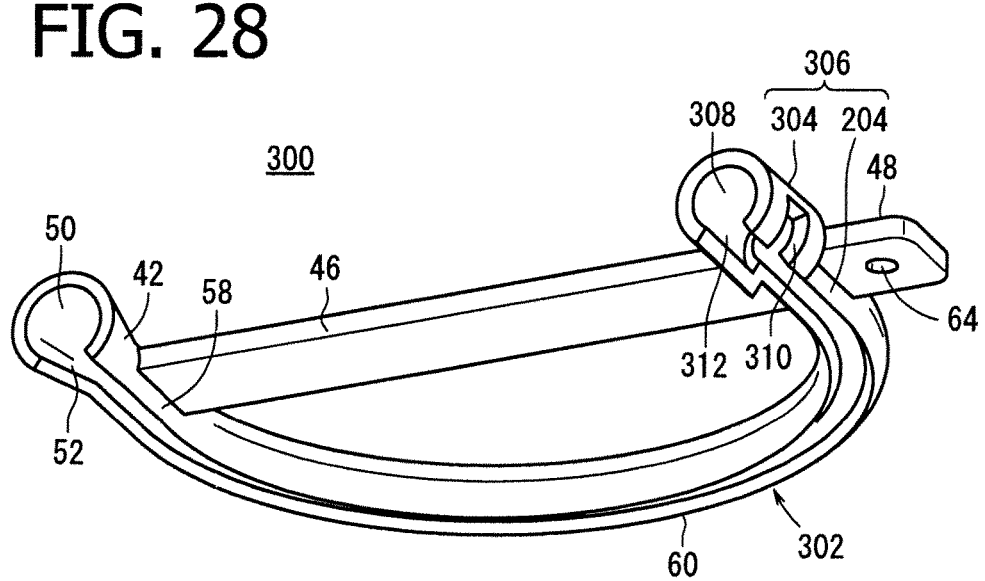
FIG. 28 is a perspective view of the direction changing device shown in FIG. 27.

As shown in FIG. 27, the medical assembly 12B according to this embodiment differs from the above-described medical apparatus assembly 12A in the configuration of direction changing device 300. Specifically, a direction changing section 302 of the direction changing device 300 includes a second mounting section 306 having a large diameter portion 304 in which the entire hub rear end section 25 of a sheath introducer 18 can be mounted.

Specifically, a third receiving bore 308 in the large diameter portion 304 is formed to correspond in shape to the hub rear end section 25. In addition, as shown in FIG. 28, a wall portion defining the third receiving bore 308 is formed with a cutout 310 in which a branch connector 35 of a branch tube 30 can be disposed. The cutout 310 communicates with the third slit 312.

According to the direction changing device 300 in this embodiment, the entire hub rear end section 25 can be mounted in the third receiving bore 308 in the large diameter portion 304. Therefore, shifting of the catheter insertion port 33 is restrained by the direction changing device 300. Consequently, the shaft 22 of the catheter 16 can be assuredly inserted into the catheter insertion port 33.

In addition, since the wall portion constituting the large diameter portion 304 is formed with the cutout 310 communicating with the third slit 312, it is ensured that at the time of mounting the hub rear end section 25 into the third receiving bore 308 in the large diameter portion 304, interference between the branch connector 35 and the large diameter portion 304 can be suitably minimized.

Fourth Embodiment

Figure 29:
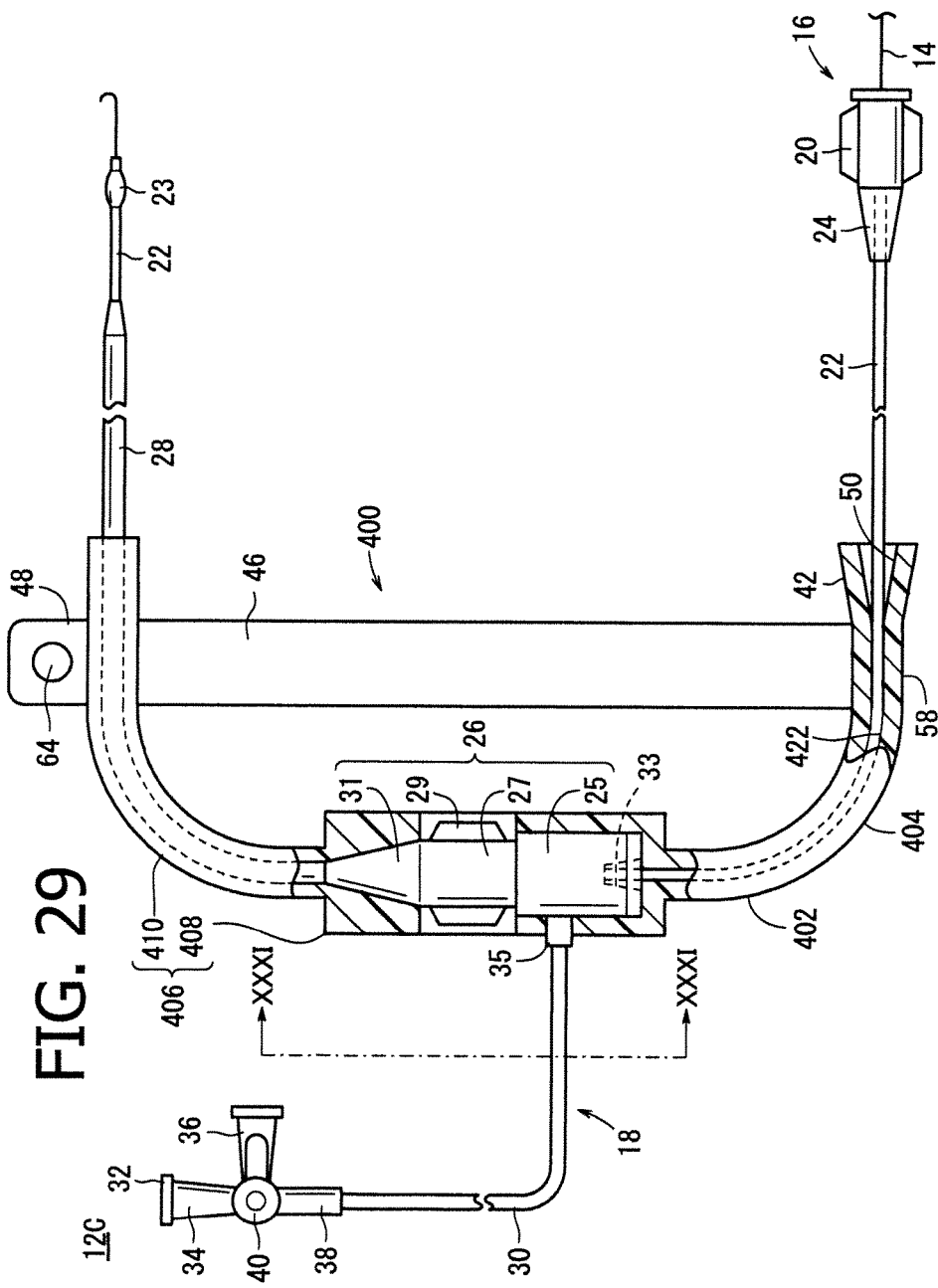
FIG. 29 is a schematic plan view of a medical assembly having a direction changing device according to a fourth embodiment of the present invention.

A medical assembly 12C according to a fourth embodiment of the present invention will be described below, referring to FIGS. 29 to 31. As shown in FIG. 29, the medical assembly 12C according to this embodiment differs from the above-described medical assembly 12A in the configuration of direction changing device 400.

Specifically, as shown in FIG. 29, a direction changing section 402 of the direction changing device 400 is formed in a roughly U-shaped form in plan view. The direction changing section 402 includes a first mounting section 58 continuous with a tapered section 42, an intermediate section 404 continuous with the first mounting section 58, and a second mounting section 406 continuous with the intermediate section 404.

The second mounting section 406 includes a large diameter portion 408 which is continuous with the intermediate section 404 and in which the sheath hub 26 of the sheath introducer 18 can be mounted, and a small diameter portion 410 which is continuous with the large diameter portion 408 and in which the sheath tube 28 can be mounted.

Figure 30:
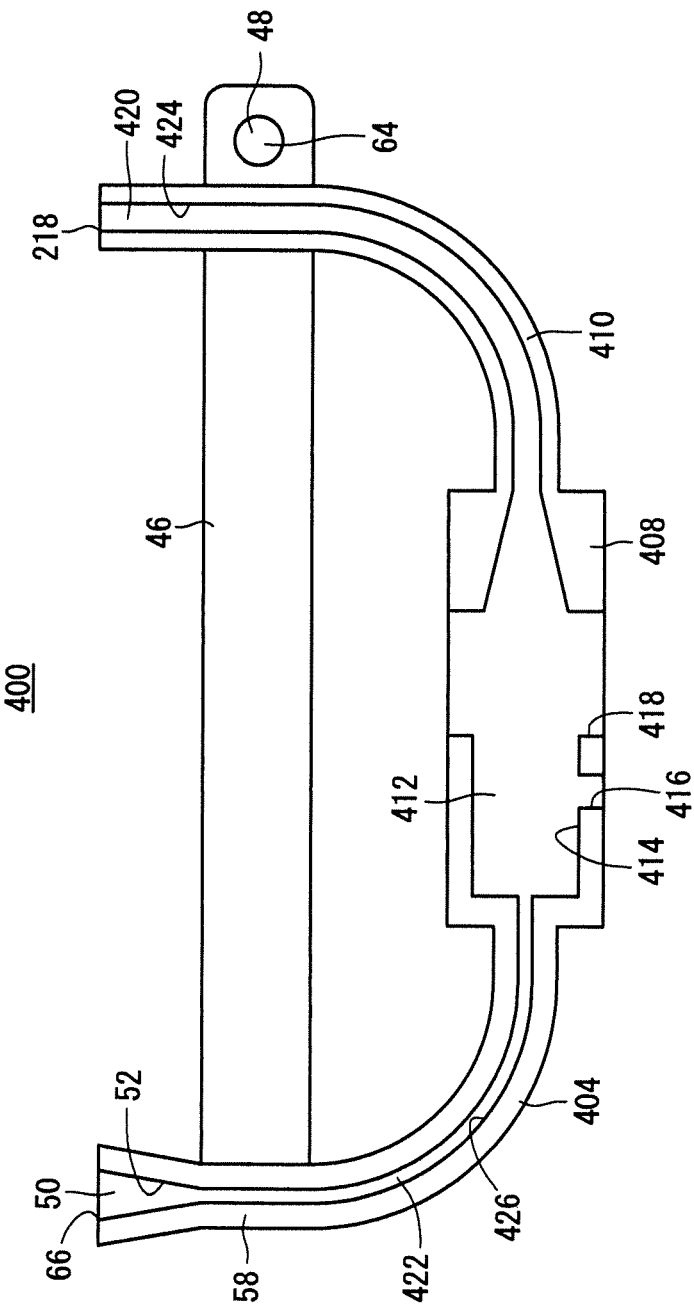
FIG. 30 is a plan view of the direction changing device shown in FIG. 29.

As shown in FIG. 30, a third receiving bore 412 and a third slit 414 of the large diameter portion 408 are formed to correspond in shape to the sheath hub 26 (a hub rear end section 25, a hub intermediate section 27, and a hub distal end section 31) of the sheath introducer 18.

Figure 31:
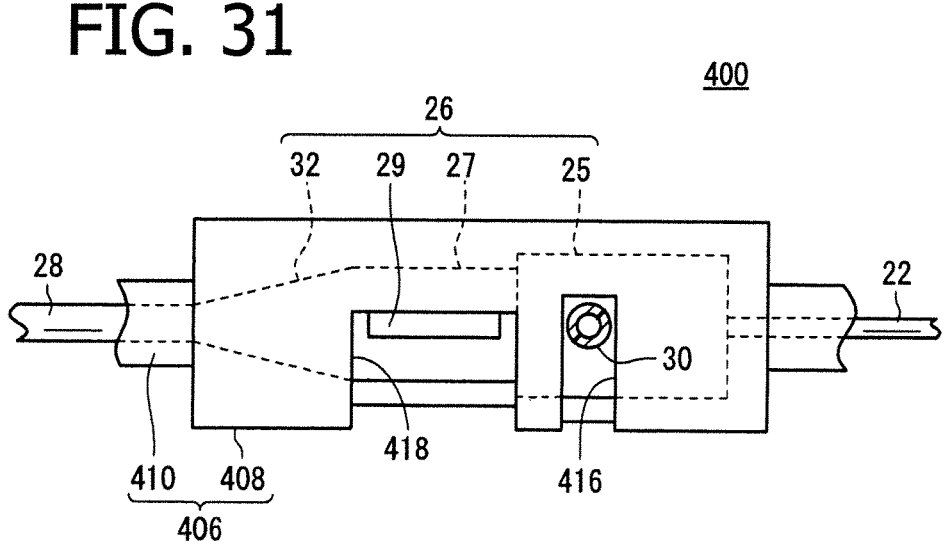
FIG. 31 is a fragmenting sectional side view taken along line XXXI-XXXI of FIG. 29.

As shown in FIG. 31, the wall portion defining the third receiving bore 412 in which the hub rear end section 25 is to be mounted is formed with a cutout 416 in which a branch connector 35 of a branch tube 30 can be disposed.

The cutout 416 communicates with a third slit 414. The wall portion defining the third receiving bore 412 in which the hub intermediate section 27 is to be mounted is formed with a cutout 418 in which a pair of projection pieces 29 formed to project from the outer circumferential surface of the hub intermediate section 27 can be disposed.

The small diameter portion 410 is a tubular member constituting an end portion of the direction changing section 402. A lumen (a fourth receiving bore 420) of the small diameter portion 410 communicates with the third receiving bore 412. Thus, in this embodiment, the first receiving bore 50, the second receiving bore 422, the third receiving bore 412 and the fourth receiving bore 420 together form a single receiving bore.

The small diameter portion 410 has a fourth slit 424 formed in its outer circumferential surface (having a constant width) communicating with the fourth receiving bore 420, over the entire length thereof (see FIG. 30). The width of the fourth slit 424 gradually narrows toward the fourth receiving bore 420. In other words, the width of the fourth slit 424 gradually decreases along the direction from the outer circumferential surface of the small diameter part 410 toward the wall surface defining the fourth receiving bore 420. The fourth slit 424 communicates with the third slit 414. Consequently, the first slit 52, the second slit 426, the third slit 414 and the fourth slit 424 together form a single slit.

According to this embodiment, the whole part of the sheath hub 26 and a part of the sheath tube 28 can be mounted to the direction changing device 400. Therefore, relative shifting of the catheter insertion port 33 and the direction changing device 400 (the second disposing hole 422) is restricted. This makes it possible to insert the shaft 22 of the catheter 16 into the catheter insertion port 33 more assuredly.

In addition, since the wall portion constituting the large diameter portion 408 is formed with the cutout 416 and the cutout 418, it is ensured that at the time of mounting the sheath hub 26 into the third receiving bore 412 in the large diameter part 408, interference of the branch connector 35 of the branch tube 30 and the pair of projection pieces 29 of the sheath hub 26 with the large diameter part 408 will be avoided.

Fifth Embodiment

Figure 32:
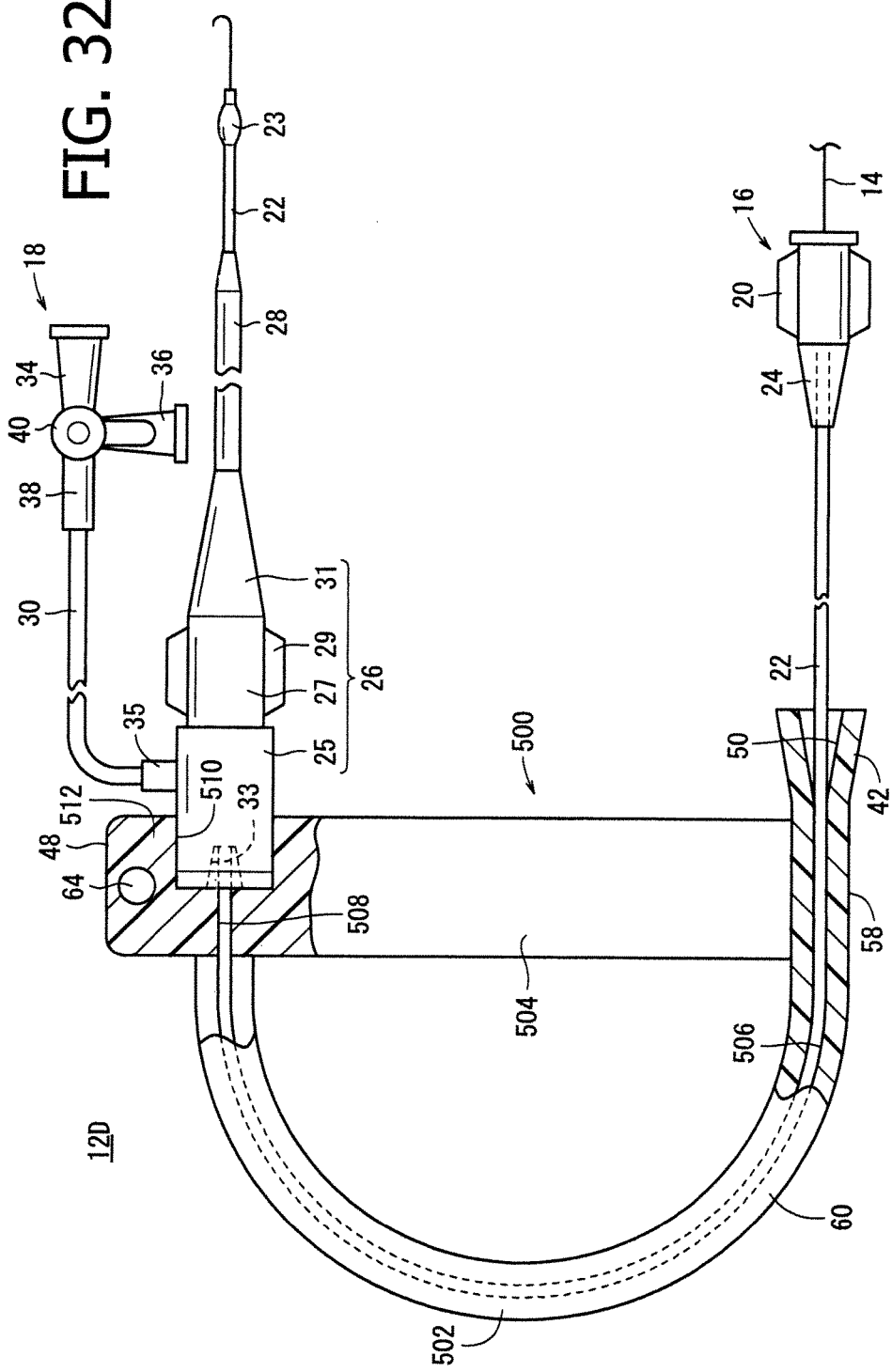
FIG. 32 is a schematic plan view of a medical assembly having a direction changing device according to a fifth embodiment of the present invention.
Figure 33:
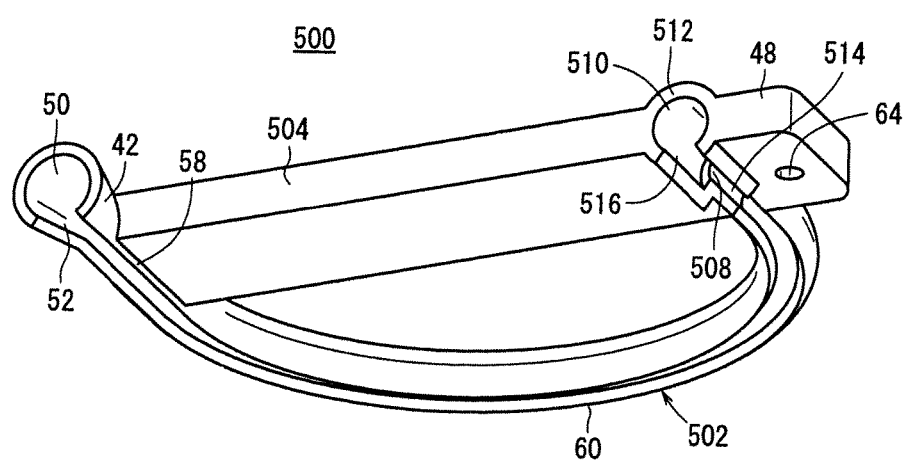
FIG. 33 is a perspective view of the direction changing device shown in FIG. 32.
Figure 34:
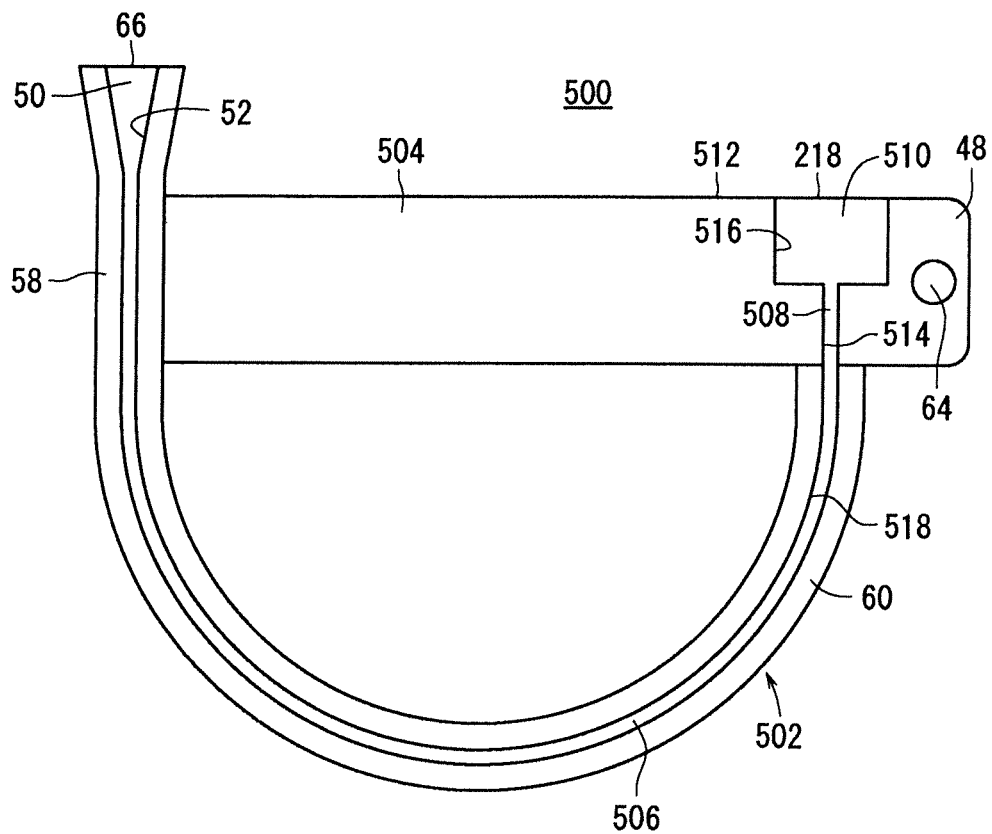
FIG. 34 is a plan view of the direction changing device shown in FIG. 32.

A medical assembly 12D according to a fifth embodiment of the present invention will be described below, referring to FIGS. 32 to 35. As shown in FIG. 32, the medical assembly 12D according to this embodiment differs from the above-described medical assembly 12A in the configuration of direction changing device 500.

Specifically, as shown in FIGS. 32 to 35, the direction changing device 500 includes a tapered section 42, a direction changing section 502, an interconnecting section 504, and a locking section 48 provided integrally with the interconnecting section 504. The direction changing section 502 includes a first mounting section 58 and an intermediate section 60, and does not include the above-mentioned second mounting section 208. The other end of the intermediate section 60 is joined to the interconnecting section 504.

The interconnecting section 504 has: an introduction bore 508 which communicates with a second receiving bore 506 in the direction changing section 502 and in which the shaft 22 of the catheter 16 is slidable; and a second mounting section 512 defining a receiving bore 510 which communicates with the introduction bore 508 and in which a portion of the hub rear end section 25 of the sheath introducer 18 can be disposed. Thus, a first receiving bore 50, the second receiving bore 506, the introduction bore 508 and the receiving bore 510 together form a single bore (see FIG. 34).

In addition, the interconnecting section 504 has a slit 514 is formed in its outer surface communicating with the introduction bore 508, and which has a constant width along the entire length thereof, and a slit 516 communicating with the receiving bore 510, and which has a constant width over the entire length thereof.

Figure 35:
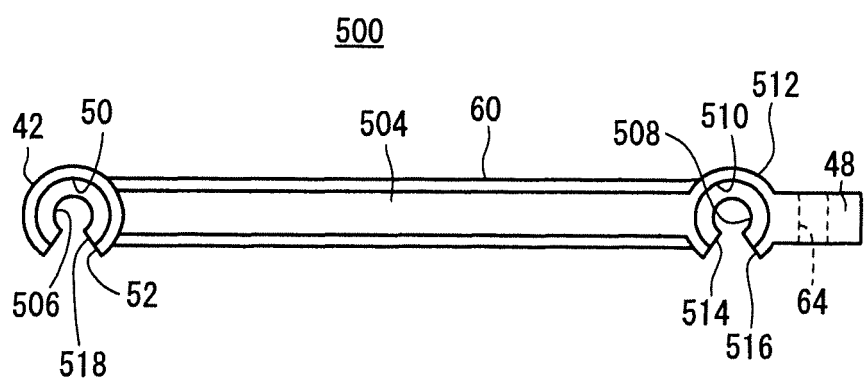
FIG. 35 is a front elevational view of the direction changing device shown in FIG. 32.

The slit 514 gradually narrows in width toward the introduction bore 508 (see FIG. 35). In other words, the width of the slit 514 gradually decreases along the radial direction from the outer surface of the interconnecting section 504 toward a wall surface defining the introduction bore 508. The slit 514 communicates with a second slit 518.

The slit 516 gradually narrows in width toward the receiving bore 510 (see FIG. 35). In other words, the width of the slit 516 gradually decreases along the radial direction from the outer surface of the interconnecting section 504 toward a wall surface defining the disposing hole 510. The slit 516 communicates with the slit 514. Thus, the first slit 52, the second slit 518, the slit 514 and the slit 516 together constitute a single slit.

The interconnecting section 504 according to this embodiment is so configured that in the condition where the hub rear end section 25 of the sheath introducer 18 is disposed in the receiving bore 510, the catheter insert port 33 of the hub rear end section 25 and the introduction bore 508 communicate with each other.

According to this embodiment, the same effect as that of the above-described direction changing device 200 can be obtained. In addition, the interconnecting section 504 is formed with the second mounting section 512 defining the receiving bore 510 and with the introduction bore 508 so that the catheter insertion hole 33 and the introduction port 508 communicate with each other in the condition where a portion of the hub rear end section 25 is disposed in the receiving bore 510. Therefore, the shaft 22 of the catheter 16 can be assuredly introduced into the catheter insertion port 33, with a simple configuration.

This embodiment is not limited to the above-described configuration. For example, the receiving bore 510 may be so formed that the entire hub rear end section 25 can be disposed therein. In that case, the interconnecting section 504 is formed with a cutout so that there is no interference between the branch connector 35 and the branch tube 30 with the interconnecting section 504.

The present invention is not restricted to the above-described embodiments, and various configurations can naturally be adopted within the scope of the gist of the invention.

The direction changing section of the direction changing device is not restricted to the configuration in which it is formed in a roughly U-shaped curved form in plan view, but may be configured in any desired shape. Specifically, for example, the direction changing section may be formed in a roughly L-shaped form in plan view. In addition, the direction changing device may be used with its slitted side on the lower side (the patient side) or on the upper side (the opposite side of the patient).

In this case, the axial direction of the first mounting section and the axial direction of the second mounting section, in the direction changing section, intersect each other. In the condition where the sheath tube is mounted in the first mounting section and the second mounting section, the sheath tube is held in a curved shape such that the sheath tube portion mounted in the first mounting section extends proximally to distally in one direction and the sheath tube portion mounted in the second mounting section extends proximally to distally in another direction with the directions being different from each other. This ensures that at the time of inserting the catheter into the sheath introducer, the catheter can be easily operated by the operator's dominant hand and, therefore, the catheter can be efficiently inserted into the living body.

What is claimed is:

1. A direction changing device for use with a flexible tubular medical device having a hub, the direction changing device comprising:

a direction changing section that includes a first mounting section, an intermediate section that is continuous with the first mounting section, and a second mounting section that is continuous with the intermediate section;

wherein the first mounting section generally extends in a first axial direction and is configured to allow a first portion of the tubular medical device to be received therein; and wherein the second mounting section generally extends in a second axial direction and is configured to allow a second portion of the tubular medical device to be received therein, the first and second mounting sections being fixed in spaced relation to each other with the first and second axial directions generally extending in a plane either transverse or parallel to each other so that with the tubular medical device portions received therein, the first and second portions will extend in either transverse or parallel directions to each other; and a tapered section that is continuous with a distal end of the first mounting section, wherein the tapered section is formed with a first receiving bore whose diameter decreases toward the direction changing section; and wherein the second mounting section has a small diameter portion and a large diameter portion that is continuous with the small diameter portion;

wherein the first mounting section, the intermediate section, and the small diameter portion are integrally formed as a tubular body having a second receiving bore;

wherein the large diameter portion has a third receiving bore in which the hub can be disposed;

wherein each of the first receiving bore and the third receiving bore is formed to be larger than the second receiving bore;

wherein each of the first, second, and third receiving bores have respective maximum diameters;

wherein the tapered section has a first slit formed in the outer circumferential surface of the tapered section which has a first opening to the first receiving bore;

wherein the tubular body has a second slit formed in the outer circumferential surface of the tubular body which has a second opening to the second receiving bore;

wherein the large diameter portion has a third slit formed in the outer circumferential surface of the large diameter potion which has a third opening to the third receiving bore;

wherein the second slit communicates with the first slit and third slit;

wherein the first slit is formed to gradually decrease in width along the radial direction from the outer circumferential surface of the tapered section toward the first receiving bore so that a width across the first opening is less than the maximum diameter of the second bore;

wherein the second slit is formed to gradually decrease in width along the radial direction from the outer circumferential surface of the tubular body toward the second receiving bore so that a width across the second opening is less than the maximum diameter of the second bore; and wherein the third slit is formed to gradually decrease in width along the radial direction from the outer circumferential surface of the large diameter potion toward the third receiving bore so that a width across the third opening is less than the maximum diameter of the third opening.

2. The direction changing device of claim 1 wherein the first and second mounting sections are configured so that with the corresponding tubular medical device first and second portions received therein, the tubular medical device adopts a curved configuration extending between the first and second mounting sections so that the first and second portions extend in parallel and in opposite directions to each other.

3. The direction changing device of claim 1 including an interconnecting section extending between the first and second mounting sections configured to fix the first and second mounting sections in spaced relation to each other.

4. The direction changing device of claim 1 wherein the intermediate section has an arcuate configuration so that the tubular medical device adopts a curved configuration when received in the arcuate intermediate section and with the first and second portions received in the corresponding first and second mounting sections.

5. The direction changing device of claim 1 wherein the slits are configured so that the tubular medical device portions are received by a snap-fit connection in the respective mounting sections.

6. The direction changing device of claim 1 in combination with the tubular medical device.

7. The direction changing device of claim 1 wherein the first, second and third bores together form a combined bore, and the first, second and third slits together form a combined slit that extends continuously along and in communication with the combined bore via the first, second and third openings thereof.

8. A medical assembly comprising:

a catheter having a shaft;

a sheath introducer having a sheath tube for being inserted into a blood vessel and for receiving the catheter shaft to be advanced into the blood vessel, and an enlarged sheath hub through which the catheter shaft can be advanced into the sheath tube;

a redirecting mechanism having a lumen configured for receiving at least one of the catheter shaft and the sheath tube therein and configured to allow an operator to direct the catheter shaft in a first direction via a first end portion of the redirecting mechanism with the catheter shaft exiting the redirecting mechanism in a second direction via a second end portion thereof for being inserted into the blood vessel, wherein the redirecting mechanism first and second end portions comprise spaced tubular portions, one of the redirecting mechanism spaced tubular portions comprises a tapered end portion that tapers down from an entry end of the redirecting mechanism to the lumen thereof for insertion of the catheter shaft through the entry end and into the lumen, and the other one of the redirecting mechanism spaced tubular portions comprises an enlarged portion for receiving the enlarged sheath hub therein, wherein the spaced tubular end portions each have a slit formed in an outer circumferential surface thereof which communicates with the lumen at a juncture therebetween and gradually decreases in width in the radial direction from the outer circumferential surface to the lumen with the lumen gradually increasing in width in the radial direction away from the juncture toward a maximum diameter thereof, connecting structure extending between the spaced tubular portions that is configured for substantially fixing the spacing between the tubular portions, and wherein at least one of the tubular portions and the connecting structure have a plurality of removable connections therebetween.

* * * * *